US007067635B2

(12) United States Patent
Marchetti et al.

(10) Patent No.: US 7,067,635 B2
(45) Date of Patent: Jun. 27, 2006

(54) NUCLEOTIDE AND DEDUCED AMINO ACID SEQUENCES OF TUMOR GENE INT6

(75) Inventors: Antonio Marchetti, Viareggio (IT); Fiamma Buttitta, Viareggio (IT); Gilbert H. Smith, Falls Church, VA (US); Robert Callahan, Alexandria, VA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/783,415

(22) Filed: Feb. 19, 2004

(65) Prior Publication Data
US 2004/0141918 A1 Jul. 22, 2004

Related U.S. Application Data

(60) Division of application No. 09/858,152, filed on May 14, 2001, now Pat. No. 6,737,251, which is a division of application No. 09/378,842, filed on Aug. 23, 1999, now Pat. No. 6,342,392, which is a division of application No. 08/875,847, filed as application No. PCT/US96/01884 on Feb. 9, 1996, now Pat. No. 6,255,105, which is a continuation-in-part of application No. 08/385,998, filed on Feb. 9, 1995, now abandoned.

(51) Int. Cl.
*C07K 16/00* (2006.01)
(52) U.S. Cl. .................. 530/387.1; 530/387.3; 530/387.7; 530/387.9; 530/388.1; 536/23.1
(58) Field of Classification Search ............. 530/388.2, 530/391.7, 387.1, 387.3, 387.7, 387.9, 388.1, 530/388.15, 350; 435/69.7, 358; 536/23.1
See application file for complete search history.

(56) References Cited

U.S. PATENT DOCUMENTS

5,194,596 A * 3/1993 Tischer et al. ............. 530/399
5,350,836 A * 9/1994 Kopchick et al. .......... 530/399

OTHER PUBLICATIONS

Pennica et al.,PNAS 95:14717-14722, 1998.*
Benjamin et al., 1998, Development 125:1591-1598.*
Vukicevic et al. (1996, PNAS USA 93:9021-9026.*
Hanash. S ,Nature Reviews, Applied Proteomics Collection, pp. 9-14,Mar. 2005.*
Hu et a l.,2003, Journal of Proteome Research 2:405-412.*
Vallejo et al .,Biochimie, 2000, vol. 82, pp. 1129-1133.*
Powell et al .,Pharmacogenesis, 1998, vol. 8, pp. 411-421.*
Fu et al .,EMBO Journal, 1996, vol. 15, pp. 4392-4401.*
Alberts et al. .,Molecular Biology of the Cell, 3rd edition, 1994, p. 465.*
Skolnick et al. 2000, Trends in Biotech. 18:34-39.*
Pilbeam et al., 1993, Bone14:717-720.*
Bork , 2000, Genome Research 10:398-400.*
Doerks et al. 1998, Trends in Genetics 14:248-250.*
Smith et al. 1997, Nature Biotechnology 15:1222-1223.*
Brenner , 1999, Trends in Genetics 15:132-133.*
Bork et al. 1996, Trends in Genetics 12:425-427.*
Bowie et al. 1990, Science 247:1306-1310.*
Guo et al., "Characterization of the Interaction between the Interferon-Induced Protein P56 and the Int6 Protein Encoded by a Locus of Insertion of the Mouse Mammary Tumor Virus," *J. Virology* 74(4):1892-1899 (Feb. 2000).
Morris et al., "Silencing of Human Int-6 impairs mitosis progression and inhibits cyclin B-Cdk1 activation," *Ocogene* 24:1203-1211 (2005).
Watkins et al., Cell cycle-related variation in subcellular localization of cIF3e/INT6 in human fibroblasts, *Cell Prolif.*, 37:149-160 (2004).
Dickson et al., *Cell* 37:529-536, 1984.
Diella et al., *10th Annual Meeting on Oncogenes*, Frederick, MD, 1994.
Diella et al., *DNA and Cell Bio.* 16:839-847, 1997.
Gallahan et al., *J. Virol.* 61(1):66-74, 1987.
Jhappen et al., *Genes & Develop.*, 6:345-355, 1992.
Marchetti et al., *7th Annual Meeting on Oncogenes*, Frederick, MD, 1991.
Marchetti et al., *J. Virol.* 69(3):1932-1938, 1995.
Miyazaki et al., *9th Annual Meeting on Oncogenes*, Frederick, MD, 1993.
Miyazaki et al., *Genomics* 27:420-424, 1995.
Muller et al., *Embo. J.* 9:907-913, 1990.
Nucleic Acid Sequence having GenBank Accession No. D11956.
Nucleic Acid Sequence having GenBank Accession No. Z25267.
Nusse et al., *Cell* 31:99-109, 1982.
Peters et al., *Proc. Natl. Acad. Sci. USA* 86:5678-5682, 1982.
Robbins et al., *J. Virol.* 66:2594-2599, 1992.
Tsukamoto et al., *Cell* 55:619-625, 1988.

* cited by examiner

*Primary Examiner*—Susan Ungar
*Assistant Examiner*—Minh-Tam Davis
(74) *Attorney, Agent, or Firm*—Klarquist Sparkman LLP

(57) ABSTRACT

The present invention discloses the isolation of the human and murine wild-type Int6 gene and the cDNAs sorresponding to these genes. The invention further describes the use of reagents derived from the nucleic acid and amino acid sequences of the Int6 gene in diagnostic methods, immunotherapy, gene therapy and as vaccines.

12 Claims, 17 Drawing Sheets

FIG. 5A

```
         10                  30                  50                  70                  90
AACAAGGCGCTCCTTCCCCGGCAAGATGGCGAGTACGACCTGACTACTGCATGCGCATTTTCTGGATCGGCACCTGGTCTTTCCGCTTCTTGAGTTT 110                 130                 150                 170                 190
CTCTCTGAAAGAGATTTATAATGAAAAGAATTATTACAAGGAAATTAGATCTTCTTAGTGATACCAATGTGTGGACTTTGCTATGGATGTTTACA
                                                                              M  V  D  F  A  M  D  V  Y  K 210                 230                 250                 270                 290
AAAACCTTTATTCTGATGATATCCCTCATGCTTTGAGAGAAAAAAGAACCAGTCTGAAACAGCTCCAGGCAGAAACAGAACCAATTGT
 N  L  Y  S  D  D  I  P  H  A  L  R  E  K  R  T (T) V  V  A  Q  L  K  Q  L  Q  A  E  T  E  P  I  V 310                 330                 350                 370                 390
GAAGATGTTTGAAGATCCAGAAACTACAAGGCAGATGCAGTCAACCAGGATGGCAGGAGATGTTATTTGACTACCTGGCAGACAAACATGGGTTTAGGCAA
 K  M  F  E  D  P  E (T) R  Q  M  Q (S) T  R  D  G  R  M  L  F  D  Y  L  A  D  K  H  G  F  R  Q 410                 430                 450                 470                 490
GAGTACTTAGATACACTCTACAGATACGCCAAAATTCCAGTGTGGAAATTACTCTGGAGCTATCTTTACTTCTTTAGAGTTTTGGTCC
 E  Y  L  D  T  L  Y  R  Y  A  K  F  Q  Y  E  C  G (N) Y  S  G  A  A  E  Y  L  Y  F  F  R  V  L  V  P 510                 530                 550                 570                 590
CAGCAACAGATAGAAATGCTTTAAGTTCGCTCTGGGGAAAACTGGCCTCTGAAATCTTAATGCAGAATTGGGATGCAGCCATGGAAGACCTTACTCGATT
 A (D) R  N  A  L  S  S  L  W  G  K  L  A  S  E  I  L  M  Q  N  W  D  A  A  M  E  D  L  T  R  L 610                 630                 650                 670                 690
AAAAGAAACCATAGACAATAATTCTGTGAGTTCTCCACTCCAGTCTCTTCAGCAGCGAACATGGCTCATTCATTGGTCTCTATTGTTTTTTCAACCAT
 K  E  T  I  D (N) N  S  V  S  S  P  L  Q  S  L  Q  Q  R  T  W  L  I  H  W  S  L  F  V  F  F  N  H 710                 730                 750                 770                 790
CCAAAGGGCCGTGATAACATTATTGATCTCTTCCTTTACCAACCACAGTATCTTAATGCAATTCAGACTATGTGTCCACATATTCTACGCTATTGACTA
 P  K  G  R  D  N  I  I  D  L  F  L  Y  Q  P  Q  Y  L  N  A  I  Q  T  M  C  P  H  I  L  R  Y  L  T  T
```

FIG. 5B

```
          810                830                850                870                890
CTGCCGTCATAACCAACAAAGATGTGCGGAAACGCCGGCAGTGCTGAAAGATCTGTGAAAGTGATTCAACAGAGTCTTACACATATAAAGACCCAAT
 A  V  I  N  K  D  V  R  K  R  R  Q  V  L  K  D  L  V  K  V  I  Q  Q  E  S  Y  K  D  P  I 910                930                950                970                990
TACAGAATTTGTTGAATGCCTATATGTTAACTTTGATTTTGACGGGGCTCAGAAAAAGCTGAGAGAATGTGAATCAGTGCTCGTGAATGACTTCTTCCTG
 T  E  F  V  E  C  L  Y  V  N  F  D  F  D  G  A  Q  K  K  L  R  E  C  E  S  V  L  V  N  D  F  F  L 1010               1030               1050               1070               1090
GTAGCGTGTCTGGAGGACTTCATTGAGAATGCCCGTCTCTTCATATTTGAGACGTTTTGTCGTATCCACCAGTGTATCAGCATTAATATGTTAGCAGATA
 V  A  C  L  E  D  F  I  E  N  A  R  L  F  I  F  E  T  F  C  R  I  H  Q  C  I  S  I  N  M  L  A  D  K 1110               1130               1150               1170               1190
AACTGAATATGACTCCAGAAGAAGCTGAAAGATGGATGCCAAGATTGATTCTAAACTAGGTCATGTGGT
 L  N  M  P  E  E  A  E  R  W  I  V  N  L  I  R  N  A  R  L  D  A  K  I  D  S  K  L  G  H  V  V 1210               1230               1250               1270               1290
AATGGGCAACAATGCAGTCTCGCCTTACCAGCAAGTGATTGAAAAGACCAAGAGCCTTTCTTTTTAGAAGCCAAATGTTGGCCATGAATATTGAAAAGAAA
 M  G  N  N  A  V  S  P  Y  Q  Q  V  I  E  K  T  K  S  L  F  R  S  Q  M  L  A  M  N  I  E  K  K 1310               1330               1350               1370               1390
CTTAATCAGAACAGTAGATCAGAGGCTCCCAACTGGGCAACCCAAGACTCTGGCTTCTATTAAAGGATTATATAAAGAAGAAAAAGGAATAAGTGAA
 L  N  Q  N  R  S  E  A  P  N  W  A  T  Q  D  S  G  F  Y 1410               1430               1450               1470               1490
AGACACAGTAGCCATTGTGTATAAAGGATGACATACATTTTTAGAAGCAATTAACATGTTGCTACAAATTTTGGAGAATTTGAATAAAATTGGCTATGA
```

FIG. 9A

TUMOR 1139

```
350
1  GATGGCAGGATGTTATTTGACTACCTGGCAGACAAACATGGGTTTAGGCAAGAGTACTTA
   D  G  R  M  L  F  D  Y  L  A  D  K  H  G  F  R  Q  E  Y  L
2  .  .  .  .  .  .  .  .  .  .  .  .  .  .  .  .  .  .  .  .

1  GATACACTCTACAGATACGCAAAATTCCAGTGTGTGGAAATTACTCTGGAGCTGCA
   D  T  L  Y  R  Y  A  K  F  Q  Y  E  C  G  N  Y  S  G  A  A
2  .  .  .  .  .  .  .  .  .  .  .  .  .  .  .  .  .  .  .  .
                                                            498
1  GAGTATCTTTACTTCTTTAGAGTTTTGaattgaagatgtattgactgtcaatggcatatt
   E  Y  L  Y  F  F  R  V  L  N  *
2  .  .  .  .  .  .  .  .  .  .  .  —  —  —  —  —  —  —  —  —

1  agaacctttaacagcacttccatcatgcacaGCTGCCGACTCGGCCCAGTCGGCCGAGGGCC
2  —  —  —  —  —  —  —  —  —  —  L  P  Q  S  A  D  L  R  A 1  ACCGGGGTCTGCGGGGGGACCCTCTGGAAGGTAATGGATAAGTGACGAGCGGAGACGGGA
2  T  G  V  C  G  G  T  L  W  K  V  M  D  K  *

1  TGGCGAACAGACACAAACACTCTTTATATCATGGTTTAGGACTGTTGCAAGTTACTCAAA
1  AATCAGCACTCTTTATATCATGGTTTAGGACTGTTGCAAGTTACTCAAA
1  AATCAGCACTCTTTATATCATGGTTTAGGACTGTTGCAAGTTACTCAAA
1  AAAAGAACATAGGAGGTTACACTGTTAGAACGCTTAGATCAAAACATTTGATACCAAACCA
1  GGTCAGGAGAACCACTCTGTCTCACATCCTCCTGTTTAAGAACAGTTTGTAACCATGAAATTA
1  TTTGAACCTTGGGAACCGCAGCAATACCTTAATATGTATCATAAACAGTCAGAGGTAATG
1  CCTTAATATGTTTTATAATATGTTCTTTGCCCCTCTTCCCTTACTTTAGGATTTATTCTCC
1  AATGTTTTATCCCTGTGCCTAAATAAA
```

FIG. 9B

TUMOR 22

```
       877
1  GAGTCTTACACATATAAAGACCCAATTACAGAATTTGTTGAATGCCTATATGTTAACTTT
2   E  S  Y  T  Y  K  D  P  I  T  E  F  V  E  C  L  Y  V  N  F
3                                        978

1  GATTTTGACGGGCTCAGAAAAGCTGAGAGAATGTGAATCATtaaaataaagttcttt
2   D  F  D  G  A  Q  K  K  L  R  E  C  E  S  L  K  I  K  F  F
3                                                          -  -

1  cagagcaagtctggaattcgatatgtaaccaagcagtcagtggattatggagatacat
2
3   -  -  -  -  -  -  -  -  -  -  -  -  -  -  -  -  -  -  -  -

1  cgTGCCGCAGTCGGCCGACCTGAGGCCACCGGGTCTGCGGGGACCCTCTGGAAGGT
2   R  A  A  V  G  R  P  E  G  H  R  G  L  R  G  D  P  L  E  G
3   Q  S  K  S  G  I  R  Y  V  N  Q  A  V  S  G  F  M  E  I  H

1  AATGGATAAGTGACGAGCGGGAGACGGGATGCCGAACAGACAAACACGAGAGACGAA
2   N  G  *
3   -  -  -

1  TGTTAGGACTGTTGCAAGTTTACTCAAAAATCAGCACTCTTTATATCATGGTTTACAT
   AAGCATTACATAAGACTTGGATAGATTCCAAAAGAACATAGGAGGTTAGAACACTCAGA
   GCTTAGATCAAAAACAGTTGATACCATGAAACCAGTTCAGGAAACCTTGTCTCCATCCTTG
   TTTAAGAACAGTTTGTAACCATGAAATTATTTGAACCTTGGGAACCGCAGCAATACCTT
   AATATGTATCATAAACAGTCAGAGGTAATGCCTTAATATGTTTTATAATATGTTCTTTGC
   CCTCCTTCCTTACTTTTAGATTTATTCTCCAATGTTTATCCCTGTGCCTAAATAAA
```

FIG. 14

| 5' | | 3' |
|---|---|---|
| accaataaagttttagtgagcacag<br>tggttatttcaaaatcactcgtgtc | EXON 1 | gtgaggggtctttgggcgc<br>cactcccccagaaacccgcg |
| ttaatcagtttctttgggga<br>aattagtcaaagaaaccct | 38bp EXON 2 | gtaagttttgtcattagaact<br>cattcaaaacagtaatcttga |
| tcttctgcattttaattag<br>agaagacgtaaaattaatc | EXON 3 | gtaaactcgtcttaatttg<br>catttgagcagaattaaaac |
| cttattttgtttctgtggcc<br>gaataaaacaaagacaccgg | 36bp EXON 4 11bp | aaaaatattttaaagttgtcatg<br>tttttataaaatttcaacagtac |
| aattacaatggggttttaaa<br>ttaatgttacccaaaattt | 42bp EXON 5 42bp | taggattcccttggttcttc<br>atcctaagggaaccaagaag |
| ttcaagagtattcacaatat<br>aagttctcataagtgttata | EXON 6 | gtgagttcgtcttttcaca<br>cactcaagcagaaaagtgt |
| agttttctttatctcaccct<br>tcaaaagaaatagagtggga | 36bp EXON 8 | gtaaaactaaaatatatattg<br>cattttgatttatatataac |
| ccgttgacttattttacag<br>ggcaactgaataaaatgtc | EXON 9 | gtaagtgtgaattttattt<br>cattcacacttaaaaataaa |
| ttgttgtatttgtacatatag<br>aacaacataaacatgtatatc | EXON 10 | gtaagaacaccgtgatttgat<br>cattcttgtggcactaaacta |
| aaaactaagttttaggccc<br>ttttgattcaaaaatccggg | 35bp EXON 11 | gtgagtattatgttagctat<br>cactcataatacaatcgata |
| ttccctgtgtttccttttag<br>aagggacacaaggaaaatc | EXON 12 | gtaagaccacacatcttctat<br>cattctggtgtgtagaagata |
| gatttcttttgcatattttag<br>ctaaagaaaacgtataaaatc | EXON 13 | tcttgctgtcagttttcttg<br>agaacgacagtcaaaagaac |

SEQUENCE LISTING

<160> NUMBER OF SEQ ID NOS: 36

<210> SEQ ID NO 1
<211> LENGTH: 1505
<212> TYPE: DNA
<213> ORGANISM: Murine INT6

<400> SEQUENCE: 1

```
aacaagcgct cctttccccc ggcaagatgg cggagtacga cctgactact cgcatcgcgc      60
attttctgga tcggcacctg gtctttccgc ttcttgagtt tctctctgtg aaagagattt     120
ataatgaaaa agaattatta caaggaaaat tagatcttct tagtgatacc aatatggtgg     180
actttgctat ggatgtttac aaaaaccttt attctgatga tatccctcat gctttgagag     240
aaaaaagaac cacagttgtt gcgcagctga aacagctcca ggcagaaaca gaaccaattg     300
tgaagatgtt tgaagatcca gaaactacaa ggcagatgca gtcaaccagg gatggcagga     360
tgttatttga ctacctggca gacaaacatg ggtttaggca agagtactta gatacactct     420
acagatacgc aaaattccag tatgagtgtg gaaattactc tggagctgca gagtatcttt     480
acttctttag agttttggtc ccagcaacag atagaaatgc tttaagttcg ctctggggaa     540
aactggcctc tgaaatctta atgcagaatt gggatgcagc catggaagac cttactcgat     600
```

-continued

| | |
|---|---|
| taaaagaaac catagacaat aattctgtga gttctccact ccagtctctt cagcagcgaa | 660 |
| catggctcat tcattggtct ctatttgttt ttttcaacca tccaagggc cgtgataaca | 720 |
| ttattgatct cttcctttac caaccacagt atcttaatgc aattcagaca atgtgtccac | 780 |
| atattctacg ctatttgact actgccgtca taaccaacaa agatgtgcgg aaacgccggc | 840 |
| aggtgctgaa agatctggtg aaagtgattc aacaggagtc ttacacatat aaagacccaa | 900 |
| ttacagaatt tgttgaatgc ctatatgtta actttgattt tgacggggct cagaaaaagc | 960 |
| tgagagaatg tgaatcagtg ctcgtgaatg acttcttcct ggtagcgtgt ctggaggact | 1020 |
| tcattgagaa tgcccgtctc ttcatatttg agacgttttg tcgtatccac cagtgtatca | 1080 |
| gcattaatat gttagcagat aaactgaata tgactccaga agaagctgaa agatggattg | 1140 |
| tgaatttgat tagaaatgcg aggttggatg ccaagattga ttctaaacta ggtcatgtgg | 1200 |
| taatgggcaa caatgcagtc tcgccctacc agcaagtgat gaaaagacc aaaagccttt | 1260 |
| cttttagaag ccaaatgttg gccatgaata ttgaaaagaa acttaatcag aacagtagat | 1320 |
| cagaggctcc caactgggca acccaagact ctggcttcta ttaaaggatt ataaagaaaa | 1380 |
| gaagaaaaag gaataagtga agacacagt agccattgtg tataaaggat gacatacatt | 1440 |
| tttagaagca attaacatgt ttgctacaaa ttttggagaa tttgaataaa attggctatg | 1500 |
| attaa | 1505 |

<210> SEQ ID NO 2
<211> LENGTH: 396
<212> TYPE: PRT
<213> ORGANISM: Murine INT6

<400> SEQUENCE: 2

```
Met Val Asp Phe Ala Met Asp Val Tyr Lys Asn Leu Tyr Ser Asp Asp
1               5                   10                  15

Ile Pro His Ala Leu Arg Glu Lys Arg Thr Thr Val Val Ala Gln Leu
            20                  25                  30

Lys Gln Leu Gln Ala Glu Thr Glu Pro Ile Val Lys Met Phe Glu Asp
        35                  40                  45

Pro Glu Thr Thr Arg Gln Met Gln Ser Thr Arg Asp Gly Arg Met Leu
    50                  55                  60

Phe Asp Tyr Leu Ala Asp Lys His Gly Phe Arg Gln Glu Tyr Leu Asp
65                  70                  75                  80

Thr Leu Tyr Arg Tyr Ala Lys Phe Gln Tyr Glu Cys Gly Asn Tyr Ser
                85                  90                  95

Gly Ala Ala Glu Tyr Leu Tyr Phe Phe Arg Val Leu Val Pro Ala Thr
            100                 105                 110

Asp Arg Asn Ala Leu Ser Ser Leu Trp Gly Lys Leu Ala Ser Glu Ile
        115                 120                 125

Leu Met Gln Asn Trp Asp Ala Ala Met Glu Asp Leu Thr Arg Leu Lys
    130                 135                 140

Glu Thr Ile Asp Asn Asn Ser Val Ser Ser Pro Leu Gln Ser Leu Gln
145                 150                 155                 160

Gln Arg Thr Trp Leu Ile His Trp Ser Leu Phe Val Phe Phe Asn His
                165                 170                 175

Pro Lys Gly Arg Asp Asn Ile Ile Asp Leu Phe Leu Tyr Gln Pro Gln
            180                 185                 190

Tyr Leu Asn Ala Ile Gln Thr Met Cys Pro His Ile Leu Arg Tyr Leu
        195                 200                 205
```

```
Thr Thr Ala Val Ile Thr Asn Lys Asp Val Arg Lys Arg Arg Gln Val
    210                 215                 220

Leu Lys Asp Leu Val Lys Val Ile Gln Gln Glu Ser Tyr Thr Tyr Lys
225                 230                 235                 240

Asp Pro Ile Thr Glu Phe Val Glu Cys Leu Tyr Val Asn Phe Asp Phe
                245                 250                 255

Asp Gly Ala Gln Lys Lys Leu Arg Glu Cys Glu Ser Val Leu Val Asn
                260                 265                 270

Asp Phe Phe Leu Val Ala Cys Leu Glu Asp Phe Ile Glu Asn Ala Arg
            275                 280                 285

Leu Phe Ile Phe Glu Thr Phe Cys Arg Ile His Gln Cys Ile Ser Ile
    290                 295                 300

Asn Met Leu Ala Asp Lys Leu Asn Met Thr Pro Glu Glu Ala Glu Arg
305                 310                 315                 320

Trp Ile Val Asn Leu Ile Arg Asn Ala Arg Leu Asp Ala Lys Ile Asp
                325                 330                 335

Ser Lys Leu Gly His Val Val Met Gly Asn Asn Ala Val Ser Pro Tyr
                340                 345                 350

Gln Gln Val Ile Glu Lys Thr Lys Ser Leu Ser Phe Arg Ser Gln Met
            355                 360                 365

Leu Ala Met Asn Ile Glu Lys Lys Leu Asn Gln Asn Ser Arg Ser Glu
    370                 375                 380

Ala Pro Asn Trp Ala Thr Gln Asp Ser Gly Phe Tyr
385                 390                 395

<210> SEQ ID NO 3
<211> LENGTH: 1500
<212> TYPE: DNA
<213> ORGANISM: Homo sapiens

<400> SEQUENCE: 3 actcccttttt ctttggcaag atggcggagt acgacttgac tactcgcatc gcgcactttt      60
tggatcggca tctagtcttt ccgcttcttg aatttctctc tgtaaaggag atatataatg     120
aaaaggaatt attacaaggt aaattggacc ttcttagtga taccaacatg gtagactttg     180
ctatggatgt atacaaaaac ctttattctg atgatattcc tcatgctttg agagagaaaa     240
gaaccacagt ggttgcacaa ctgaaacagc ttcaggcaga aacagaacca attgtgaaga     300
tgtttgaaga tccagaaact acaaggcaaa tgcagtcaac cagggatggt aggatgctct     360
ttgactacct ggcggacaag catggtttta ggcaggaata tttagataca ctctacagat     420
atgcaaaatt ccagtacgaa tgtgggaatt actcaggagc agcagaatat ctttatttt      480 ttagagtgct ggttccagca acagatagaa atgctttaag ttcactctgg ggaaagctgg     540
cctctgaaat cttaatgcag aattgggatg cagccatgga agaccttaca cggttaaaag     600
agaccataga taataattct gtgagttctc cacttcagtc tcttcagcag agaacatggc     660
tcattcactg gtctctgttt gttttcttca atcaccccaa aggtcgcgat aatattattg     720
acctcttcct ttatcagcca caatatctta atgcaattca gacaatgtgt ccacacattc     780 ttcgctatt gactacagca gtcataacaa acaaggatgt tcgaaaacgt cggcaggttc      840
taaaagatct agttaaagtt attcaacagg agtcttacac atataaagac ccaattacag     900
aatttgttga atgttttata gttaactttg actttgatgg ggctcagaaa agctgagggg     960
aatgtgaatc agtgccttgtg aatgacttct tcttggtggc ttgtcttgag gatttcattg    1020
aaaatgcccg tctcttcata tttgagactt tctgtcgcat ccaccagtgt atcagcatta    1080
```

-continued

```
acatgttggc agataaattg aacatgactc cagaagaagc tgaaaggtgg attgtaaatt   1140
tgattagaaa tgcaagactg gatgccaaga ttgattctaa attaggtcat gtggttatgg   1200
gtaacaatgc agtctcaccc tatcagcaag tgattgaaaa gaccaaaagc ctttccttta   1260
gaagccagat gttggccatg aatattgaga agaaacttaa tcagaatagc aggtcagagg   1320
ctcctaactg ggcaactcaa gattctggct tctactgaag aaccataaag aaaagatgaa   1380
aaaaaaaact atcaaagaaa gatgaaataa taaaactatt atataagggg tgacttacat   1440
tttggaaaca acatattacg tataaatttt gaagaattgg aataaaattg attcatttta   1500
```

<210> SEQ ID NO 4
<211> LENGTH: 396
<212> TYPE: PRT
<213> ORGANISM: Homo sapiens

<400> SEQUENCE: 4

```
Met Val Asp Phe Ala Met Asp Val Tyr Lys Asn Leu Tyr Ser Asp Asp
  1               5                  10                  15

Ile Pro His Ala Leu Arg Glu Lys Arg Thr Thr Val Val Ala Gln Leu
             20                  25                  30

Lys Gln Leu Gln Ala Glu Thr Glu Pro Ile Val Lys Met Phe Glu Asp
         35                  40                  45

Pro Glu Thr Thr Arg Gln Met Gln Ser Thr Arg Asp Gly Arg Met Leu
     50                  55                  60

Phe Asp Tyr Leu Ala Asp Lys His Gly Phe Arg Gln Glu Tyr Leu Asp
 65                  70                  75                  80

Thr Leu Tyr Arg Tyr Ala Lys Phe Gln Tyr Glu Cys Gly Asn Tyr Ser
                 85                  90                  95

Gly Ala Ala Glu Tyr Leu Tyr Phe Phe Arg Val Leu Val Pro Ala Thr
            100                 105                 110

Asp Arg Asn Ala Leu Ser Ser Leu Trp Gly Lys Leu Ala Ser Glu Ile
        115                 120                 125

Leu Met Gln Asn Trp Asp Ala Ala Met Glu Asp Leu Thr Arg Leu Lys
    130                 135                 140

Glu Thr Ile Asp Asn Asn Ser Val Ser Ser Pro Leu Gln Ser Leu Gln
145                 150                 155                 160

Gln Arg Thr Trp Leu Ile His Trp Ser Leu Phe Val Phe Phe Asn His
                165                 170                 175

Pro Lys Gly Arg Asp Asn Ile Ile Asp Leu Phe Leu Tyr Gln Pro Gln
            180                 185                 190

Tyr Leu Asn Ala Ile Gln Thr Met Cys Pro His Ile Leu Arg Tyr Leu
        195                 200                 205

Thr Thr Ala Val Ile Thr Asn Lys Asp Val Arg Lys Arg Arg Gln Val
    210                 215                 220

Leu Lys Asp Leu Val Lys Val Ile Gln Gln Glu Ser Tyr Thr Tyr Lys
225                 230                 235                 240

Asp Pro Ile Thr Glu Phe Val Glu Cys Leu Tyr Val Asn Phe Asp Phe
                245                 250                 255

Asp Gly Ala Gln Lys Lys Leu Arg Glu Cys Glu Ser Val Leu Val Asn
            260                 265                 270

Asp Phe Phe Leu Val Ala Cys Leu Glu Asp Phe Ile Glu Asn Ala Arg
        275                 280                 285

Leu Phe Ile Phe Glu Thr Phe Cys Arg Ile His Gln Cys Ile Ser Ile
    290                 295                 300
```

```
Asn Met Leu Ala Asp Lys Leu Asn Met Thr Pro Glu Glu Ala Glu Arg
305                 310                 315                 320

Trp Ile Val Asn Leu Ile Arg Asn Ala Arg Leu Asp Ala Lys Ile Asp
            325                 330                 335

Ser Lys Leu Gly His Val Val Met Gly Asn Asn Ala Val Ser Pro Tyr
            340                 345                 350

Gln Gln Val Ile Glu Lys Thr Lys Ser Leu Ser Phe Arg Ser Gln Met
            355                 360                 365

Leu Ala Met Asn Ile Glu Lys Lys Leu Asn Gln Asn Ser Arg Ser Glu
        370                 375                 380

Ala Pro Asn Trp Ala Thr Gln Asp Ser Gly Phe Tyr
385                 390                 395
```

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 5
accaataaag ttttagtgag cacag                                    25

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
gcgcccaaag accccctcac                                          20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
ttaatcagtt tctttgggga                                          20

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 8
agtttctaat gacaaaactt ac                                       22

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9
tcttctgcat ttttaattag                                          20

-continued

```
<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
caaaattaag acgagtttac                                              20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
cttattttgt ttctgtggcc                                              20

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 12
catgacaact ttaaatatt ttt                                           23

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 13
aattacaatg gggttttaaa                                              20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
gaagaaccaa gggaatccta                                              20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15
ttcaagagta ttcacaatat                                              20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer
```

<400> SEQUENCE: 16
tgtgaaaaag acgaactcac					20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 17
agttttcttt atctcaccct					20

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 18
caatatatat tttagttttta c					21

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
ccgttgactt attttacag					20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
aaataaaaat tcacacttac					20

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 21
ttgttgtatt tgtacatata g					21

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 22
atcaaatcac ggtgttctta c					21

```
<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
aaaactaagt ttttaggccc                                              20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 24
atagctaaca taatactcac                                              20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
ttccctgtgt ttccttttag                                              20

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 26
atagaagatg tgtggtctta c                                            21

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 27
gatttctttt tgcatatttt ag                                           22

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 28
caagaaaact gacagcaaga                                              20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 29
tgtccacata ttctacgcta                                              20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 30
tgtatgtcat cctttataca                                              20

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 31
gtgaaaatga catgaaattt cag                                          23

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 32
tgcagtgtga caatatgggc                                              20

<210> SEQ ID NO 33
<211> LENGTH: 687
<212> TYPE: DNA
<213> ORGANISM: Mus musculus tumor 1139

<400> SEQUENCE: 33
gatggcagga tgttatttga ctacctggca gacaaacatg ggtttaggca agagtactta     60
gatacactct acagatacgc aaaattccag tatgagtgtg gaaattactc tggagctgca    120
gagtatcttt acttctttag agttttgaat tgaagatgta ttgactgtca atggcatatt    180 agaacccttta acagcacttt ccatcatgca cagctgccgc agtcggccga cctgagggcc    240
accggggtct gcgggggac cctctggaag gtaatggata agtgacgagc ggagacggga     300
tggcgaacag acacaaacac acgagagacg aatgttagga ctgttgcaag tttactcaaa    360
aatcagcact ctttatatca tggtttacat aagcatttac ataagacttg gatagattcc    420
aaaagaacat aggaggttag aacactcaga gctagatca aaacatttga taccaaacca     480
ggtcaggaaa ccacttgtct cacatccttg ttttaagaac agtttgtaac catgaaatta    540
tttgaacctt gggaaccgca gcaataacct aatatgtatc ataaacagtc agaggtaatg    600
ccttaatatg ttttataata tgttctttgc cctcttcctt acttttagga tttattctcc    660
aatgttttat ccctgtgcct aaataaa                                        687

<210> SEQ ID NO 34
<211> LENGTH: 23
<212> TYPE: PRT
<213> ORGANISM: Mus musculus tumor 1139
```

-continued

```
<400> SEQUENCE: 34

Leu Pro Gln Ser Ala Asp Leu Arg Ala Thr Gly Val Cys Gly Gly Thr
1               5                   10                  15

Leu Trp Lys Val Met Asp Lys
            20

<210> SEQ ID NO 35
<211> LENGTH: 657
<212> TYPE: DNA
<213> ORGANISM: Mus musculus tumor 22

<400> SEQUENCE: 35
gagtcttaca catataaaga cccaattaca gaatttgttg aatgcctata tgttaacttt      60
gattttgacg gggctcagaa aaagctgaga gaatgtgaat cattaaaaat aaagttcttt     120
cagagcaagt ctggaattcg atatgtaaac caagcagtca gtggatttat ggagatacat     180
cgtgccgcag tcggccgacc tgaggccac cggggtctgc gggggaccc tctggaaggt      240 aatggataag tgacgagcgg agacgggatg gcgaacagac acaaacacac gagagacgaa     300
tgttaggact gttgcaagtt tactcaaaaa atcagcactc ttttatatca tggtttacat     360
aagcatttac ataagacttg gatagattcc aaaagaacat aggaggttag aacactcaga     420
gcttagatca aaacatttga taccaaacca ggtcaggaaa ccacttgtct cacatccttg     480
ttttaagaac agtttgtaac catgaaatta tttgaacctt gggaaccgca gcaatacctt     540
aatatgtatc ataaacagtc agaggtaatg ccttaatatg ttttataata tgttctttgc     600
cctcttcctt acttttagga tttattctcc aatgttttat ccctgtgcct aaataaa       657

<210> SEQ ID NO 36
<211> LENGTH: 21
<212> TYPE: PRT
<213> ORGANISM: Mus musculus tumor 22

<400> SEQUENCE: 36

Ala Ala Val Gly Arg Pro Glu Gly His Arg Gly Leu Arg Gly Asp Pro
1               5                   10                  15

Leu Glu Gly Asn Gly
            20
```

NUCLEOTIDE AND DEDUCED AMINO ACID SEQUENCES OF TUMOR GENE INT6

CROSS REFERENCE TO RELATED APPLICATIONS

This is a divisional of U.S. application Ser. No. 09/858,152, filed May 14, 2001, now U.S. Pat. No. 6,737,251, which is a division of U.S. application Ser. No. 09/378,842, filed Aug. 23, 1999, now issued as U.S. Pat. No. 6,342,392, which is a divisional of U.S. application Ser. No. 08/875,847, filed Sep. 25, 1997, now issued as U.S. Pat. No. 6,255,105, which is the national stage under § 371 of PCT Application No. PCT/US96/01884, filed Feb. 9, 1996, published in English under PCT Article 21(2). PCT Application No. PCT/US96/01884 is a continuation-in-part of U.S. application Ser. No. 08/385,998, filed Feb. 9, 1995, now abandoned.

FIELD OF INVENTION

The present invention relates to the area of cancer diagnostics and therapeutics. More specifically, the invention relates to the Int6 gene and to the use of reagents derived from the nucleic acid and deduced amino acid sequences of the Int6 gene in gene therapy, vaccines, diagnostic methods and immunotherapy.

BACKGROUND OF INVENTION

The mouse mammary tumor virus (MMTV) is a retrovirus which has been shown to act as an insertional mutagen that causes the deregulation of expression of cellular genes adjacent to the site of MMTV integration in mammary tumors (Varmus, H. E. (1982). *Cancer Surv.*, 1:309–320). Mice infected with MMTV frequently develop preneoplastic hyperplastic alveolar nodules (HAN) (Daniel, C., et al. *Proc. Natl. Acad. Sci. USA.*, 61:53–60; DeOme, K. B., (1959) *J. Natl. Cancer Inst.*, 78:751–757; Medina, D., (1973) *Methods Cancer Res.*, 7:3–53; Smith, G., et al. (1984) *Cancer Res.*, 44:3426–3437) and the passage of these nodules in cleared mammary fat pads of syngeneic mice by serial outgrowth often results in the development of mammary tumors within these mice in a stochastic manner. In addition, it is not uncommon to find metastatic lesions in the lungs of mice bearing outgrowths with mammary tumors. For these reasons, there is considerable interest in identifying MMTV-induced mutational events that may contribute to different stages of tumor development.

Using the MMTV genome as a molecular tag, five loci (Wnt-1/Int-1, Fgf-3/Int-2, Int-3, Wnt-3, and Fgf-4/Hst/k-FGF) have been identified which represent common integration sites (designated Int loci) for MMTV in mouse mammary tumors (Dickson, C., et al. (1984) *Cell.*, 37:529–536; Gallahan, D., et al. (1987) *J. Virol.*, 61:218–220; Nusse, R., et al. (1982) *Cell.*, 31:99–109; Peters, G., et al. (1989) *Proc. Natl. Acad. Sci. USA.*, 86:5678–5682). Transgenic mouse studies utilizing transgenes in which the MMTV LTR was linked to either the WNT-1, Fgf-3, or Int-3 genes have demonstrated that activation of expression of these genes contributes to mammary tumor-l-genesis (Jhappan, C., et al. (1992) *Genes & Develop.*, 6:345–355; Muller, W. J., et al. (1990) *Embo J.*, 9:907–913; Tsukamoto, A. S., et al. (1988) *Cell.*, 55:619–625).

The present invention describes the isolation of a new Int gene designated Int6 and the use of the gene, its gene product, and reagents derived from the gene and its gene product, in diagnostic methods, vaccines, immunotherapy and gene therapy.

SUMMARY OF INVENTION

The present invention relates to the isolation of the Int6 gene. The invention also relates to the murine and human cDNAs which comprise the coding sequence of the Int6 gene. The invention further relates to nucleic acid sequences derived from the Int6 gene and the Int6 cDNAs and the use of these nucleic acid sequences as probes to isolate homologues of the Int6 gene in other mammals or as probes to detect mutations of the Int6 gene.

It is also an object of the present invention to provide synthetic nucleic acid sequences capable of directing production of recombinant Int6 protein and peptide fragments derived therefrom, as well as equivalent natural nucleic acid sequences. Such natural nucleic acid sequences may be isolated from a cDNA or genomic library from which the gene capable of directing the synthesis of the Int6 protein may be identified and isolated. For the purposes of this application, nucleic acid sequence refer to RNA, DNA, cDNA or any synthetic variant thereof.

The present invention further relates to Int6 protein and peptides derived therefrom.

The invention also relates to antibodies directed against Int6 protein or peptides derived therefrom.

The invention also provides methods for detecting mutations of Int6 gene where detection of such mutations is useful in determining the presence of a neoplastic tissue in a subject or a genetic predisposition to cancer in a subject.

A first method for detecting mutations of the Int6 gene comprises analyzing DNA of a subject for mutations of the Int6 gene.

A second method for detecting mutations of the Int6 gene comprises analyzing RNA of a subject for alterations in the Int6 mRNA expression.

Yet another method for detecting mutations of the Int6 gene comprises analyzing protein of a subject for alterations in Int6 protein expression.

The present invention also provides pharmaceutical compositions for use as vaccines for immunizing a subject against cancer and for use in immunotherapy methods. One such composition comprises nucleic acid sequence capable of directing host organism synthesis of Int6 protein or peptide fragments thereof while a second pharmaceutical composition comprises Int6 protein or peptides derived therefrom.

The above pharmaceutical compositions may also be used in immunotherapy methods for treating a subject having cancer. For use in immunotherapy, the present invention further provides a third pharmaceutical composition comprising antibodies directed against Int6 protein or peptides derived therefrom where such antibodies are coupled to toxin molecules, radioisotopes or drugs.

The present invention therefore relates to application of immunotherapy to subjects having cancer comprising administering one or more of the above pharmaceutical compositions to said subject in a therapeutically effective amount.

The invention further relates to a method for treating a subject having cancer comprising:
(a) immunizing the subject with an amount of an expression vector encoding Int6 protein or with Int6 protein itself, said amount effective to elicit a specific T cell response;

(b) isolating said T cells from said immunized subject; and (c) administering said T cells to said immunized subject or to an unimmunized subject in a therapeutically effective amount.

The invention also provides a diagnostic kit for determining the nucleotide sequence of Int6 alleles by the polymerase chain reaction, said kit comprising purified and isolated nucleic acid sequences useful as PCR primers. These PCR primers are also useful in analyzing DNA or RNA of a subject for mutations of the Int6 gene.

The present invention further provides a method for supplying the wild-type Int6 gene to a cell having altered expression of the Int6 protein by virtue of a mutation in the Int6 gene, the method comprising: introducing a wild-type Int6 gene into a cell having altered expression of the Int6 protein such that said wild-type gene is expressed in the cell.

DESCRIPTION OF FIGURES

In FIG. 1A, the DNAs analyzed were isolated from a CZZ-1 pre-neoplastic hyperplastic outgrowth line designated CZZ-1 HOG (lane 1) and from CZZ-1 derived mammary tumors 22 (lane 2), 1262 (lane 3), 1263 (lane 4), 20 (lane 5), 19 (lane 6), 23 (lane 7), 21 (lane 8) 24 (lane 9), 8 (lane 10), 9 (lane 11), 12 (lane 12), 13 (lane 13) and 14 (lane 14) as indicated at the top of FIG. 1A. In FIG. 1B, the DNAs analyzed were isolated from CZZ-1 derived tumor 4973 (lane 1) and from 11 independent lung metastasis (lanes 2–12) from a mouse bearing tumor 4973 as indicated at the top of FIG. 1B.

FIG. 5 shows the complete nucleotide sequence of the murine 1.4 kb Int6 cDNA (SEQ ID NO: 1) where intron breaks are indicated by small arrows (▲) above the start of the next exon and the deduced amino acid sequence of the gene product is given below the nucleotide sequence. Potential phosphorylation sites for cyclic AMP/cyclic GMP-dependent protein kinase (○), protein kinase C (Δ), tyrosine kinases (–), casein kinase II (◇), and glycosylation sites (□) are indicated in the deduced amino acid sequence. Abbreviations for amino acid residues: A, Ala; C, Cys; D, Asp; E, Glu; F, Phe; G, Gly; H, His; I, Ile; K, Lys; M. Met

FIGS. 9A and 9B show the nucleotide sequences of the junctions between MMTV and Int6 sequences in chimeric Int6-MMTV LTR RNA species detected in tumors 1139 (FIG. 9A) and 22 (FIG. 9B). In FIG. 9A, the nucleotide sequence shown (SEQ ID NO: 33) begins at the 5' end of exon with the nucleotide sequence shown in lower case letters corresponding to intro 5 sequences (nucleotides 148–212 of SEQ ID NO: 33). Amino acid sequences in RNA species 2 which are identical to those in RNA species 1 are indicated by dots (see amino acids 60–108 of SEQ ID NO: 4), and nucleotide sequence which have been spliced out in RNA species 2 are indicated by dashes (see nucleotides 148–213 of SEQ ID NO: 33). Nucleotide and amino acid sequences which are underlined are from the integrated MMTV genome (nucleotides 214–687 of SEQ ID NO: 33 and SEQ ID NO: 34. respectively).

In FIG. 9B, the nucleotide sequence shown (SEQ ID NO: 35) for the chimeric RNA species detected in tumor 22 begins at the 5' end of exon 9 and run through a portion of intron 9 to the cryptic poly A addition signal in the MMTV genome. Intron nucleotide sequence is given in lower case letter (corresponding to nucleotides 103–182 of SEQ ID NO: 35), MMTV sequences are underlined (corresponding to nucleotides 183–657 of SEQ ID NO: 35), and dashes indicate nucleotide sequences of the intron which have been spliced out (corresponding to nucleotides 103–120 of SEQ ID NO: 35). The MMTV amino acid sequences are underlined (represented by SEQ ID NO: 36.) Dots correspond to amino acid residues encoded by RNA species 2 and 3 which are identical to those encoded by RNA species 1 (see also amino acids 253–268 of SEQ ID NO: 4). The abbreviations for amino acids shown in FIGS. 9A and 9B are the same as those given in the legend for FIG. 5.

FIG. 14 shows the nucleotide sequences bounding 12 of the 13 human Int6 exons (SEQ ID NOs: 5–28). Nucleotide sequences of primers (underlined) complementary to nucleic acid sequences (not underlined) bounding each exon are shown to the left and right of each exon. The upper nucleic acid sequences shown to the left and right of each exon are in the 5' to 3' orientation (SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 SEQ ID NO: 25 and SEQ ID NO: 27) while lower sequences shown to the left and right of each exon are in the 3' to 5' orientation (SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 SEQ ID NO: 26 and SEQ ID NO: 28). When the sequences bounding each exon do not begin at the intron-exon junction, the distance of the sequence from the junction is given in base pairs to the left or right of each exon.

DESCRIPTION OF INVENTION

Figure 1A:
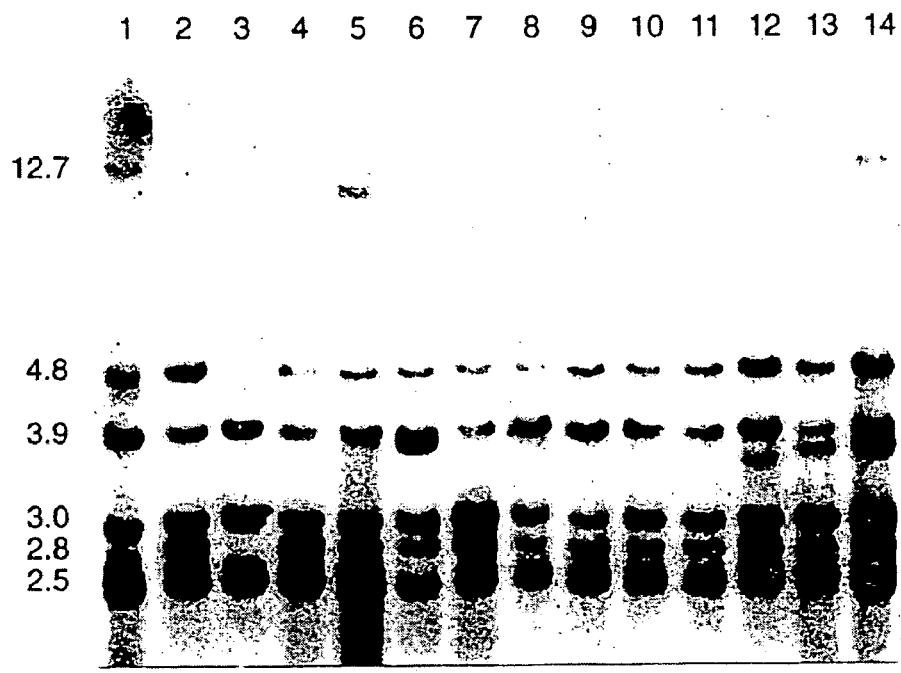
FIGS. 1A and 1B show the results of Southern blot analyses in which 10 micrograms of cellular DNA was digested by EcoRI, separated by agarose gel electrophoresis, and hybridized with MMTV LTR probe.

The present invention discloses that mutational events associated with MMTV integration into the host cell genome in tumorigenesis occur in a previously unknown gene designated Int6. This gene is located on mouse chromosome 15. More specifically, the present invention relates to Int6 gene and its corresponding cDNA. The region of mouse chromosome 15 containing the Int6 is represented in the four overlapping lambda clones (designated 1–4 in FIG. 3) and comprises the entire Int6 gene. The Int6 gene represents the wild-type Int6 gene.

The present invention is also directed to the full-length cDNA corresponding to the murine Int6 gene. This cDNA sequence is set forth below as SEQ ID NO:1.

```
AACAAGCGCT CCTTTCCCCC GGCAAGATGG CGGAGTACGA    40
CCTGACTACT GCATCGCGCA TTTTCTGGAT CGGCACCTGG    80
TCTTTCCGCT TCTTGAGTTT CTCTCTGTGA AAGAGATTTA   120
TAATGAAAAA GAATTATTAC AAGGAAAATT AGATCTTCTT   160
AGTGATACCA ATATGGTGGA CTTTGCTATG GATGTTTACA   200
AAAACCTTTA TTCTGATGAT ATCCCTCATG CTTTGAGAGA   240
AAAAAGAACC ACAGTTGTTG CGCAGCTGAA ACAGCTCCAG   280
GCAGAAACAG AACCAATTGT GAAGATGTTT GAAGATCCAG   320
AAACTACAAG GCAGATGCAG TCAACCAGGG ATGGCAGGAT   360
GTTATTTGAC TACCTGGCAG ACAAACATGG GTTTAGGCAA   400
GAGTACTTAG ATACACTCTA CAGATACGCA AAATTCCAGT   440
ATGAGTGTGG AAATTACTCT GGAGCTGCAG AGTATCTTTA   480
CTTCTTTAGA GTTTTGGTCC CAGCAACAGA TAGAAATGCT   520
TTAAGTTCGC TCTGGGGAAA ACTGGCCTCT GAAATCTTAA   560
TGCAGAATTG GGATGCAGCC ATGGAAGACC TTACTCGATT   600
AAAAGAAACC ATAGACAATA ATTCTGTGAG TTCTCCACTC   640
CAGTCTCTTC AGCAGCGAAC ATGGCTCATT CATTGGTCTC   680
TATTTGTTTT TTTCAACCAT CCAAAGGGCC GTGATAACAT   720
TATTGATCTC TTCCTTTACC AACCACAGTA TCTTAATGCA   760
ATTCAGACAA TGTGTCCACA TATTCTACGC TATTTGACTA   800
CTGCCGTCAT AACCAACAAA GATGTGCGGA AACGCCGGCA   840
GGTGCTGAAA GATCTGGTGA AAGTGATTCA ACAGGAGTCT   880
TACACATATA AAGACCCAAT TACAGAATTT GTTGAATGCC   920
TATATGTTAA CTTTGATTTT GACGGGGCTC AGAAAAAGCT   960
GAGAGAATGT GAATCAGTGC TCGTGAATGA CTTCTTCCTG  1000
GTAGCGTGTC TGGAGGACTT CATTGAGAAT GCCCGTCTCT  1040
TCATATTTGA GACGTTTTGT CGTATCCACC AGTGTATCAG  1080
```

```
CATTAATATG TTAGCAGATA AACTGAATAT GACTCCAGAA    1120

GAAGCTGAAA GATGGATTGT GAATTTGATT AGAAATGCGA    1160

GGTTGGATGC CAAGATTGAT TCTAAACTAG GTCATGTGGT    1200

AATGGGCAAC AATGCAGTCT CGCCCTACCA GCAAGTGATT    1240

GAAAAGACCA AAAGCCTTTC TTTTAGAAGC CAAATGTTGG    1280

CCATGAATAT TGAAAAGAAA CTTAATCAGA ACAGTAGATC    1320

AGAGGCTCCC AACTGGGCAA CCCAAGACTC TGGCTTCTAT    1360

TAAAGGATTA TAAAGAAAAG AAGAAAAAGG AATAAGTGAA    1400

AGACACAGTA GCCATTGTGT ATAAAGGATG ACATACATTT    1440

TTAGAAGCAA TTAACATGTT TGCTACAAAT TTTGGAGAAT    1480

TTGAATAAAA TTGGCTATGA TTAA                    1504
```

The abbreviation used for the nucleotides are those standardly used in the art.

The deduced amino acid sequence of the murine Int6 cDNA is shown as SEQ ID NO:2 below and starts at nucleotide 173 of SEQ ID NO:1 and extends 1188 nucleotides.

```
Met Val Asp Phe Ala Met Asp Val Tyr Lys Asn Leu
 1               5                  10

Tyr Ser Asp Asp Ile Pro His Ala Leu Arg Glu Lys
             15                  20

Arg Thr Val Val Ala Gln Leu Lys Gln Leu Gln
 25                  30                  35

Ala Glu Thr Glu Pro Ile Val Lys Met Phe Glu Asp
             40                  45

Pro Glu Thr Thr Arg Gln Met Gln Ser Thr Arg Asp
     50                  55                  60

Gly Arg Met Leu Phe Asp Tyr Leu Ala Asp Lys His
             65                  70

Gly Phe Arg Gln Glu Tyr Leu Asp Thr Leu Tyr Arg
         75                  80

Tyr Ala Lys Phe Gln Tyr Glu Cys Gly Asn Tyr Ser
 85                  90                  95

Gly Ala Ala Glu Tyr Leu Tyr Phe Phe Arg Val Leu
             100                 105

Val Pro Ala Thr Asp Arg Asn Ala Leu Ser Ser Leu
     110                 115                 120

Trp Gly Lys Leu Ala Ser Glu Ile Leu Met Gln Asn
             125                 130

Trp Asp Ala Ala Met Glu Asp Leu Thr Arg Leu Lys
             135                 140

Glu Thr Ile Asp Asn Asn Ser Val Ser Ser Pro Leu
 145                 150                 155

Gln Ser Leu Gln Gln Arg Thr Trp Leu Ile His Trp
             160                 165

Ser Leu Phe Val Phe Asn His Pro Lys Gly Arg
     170                 175                 180

Asp Asn Ile Ile Asp Leu Phe Leu Tyr Gln Pro Gln
             185                 190

Tyr Leu Asn Ala Ile Gln Thr Met Cys Pro His Ile
             195                 200

Leu Arg Tyr Leu Thr Thr Ala Val Ile Thr Asn Lys
 205                 210                 215

Asp Val Arg Lys Arg Gln Val Leu Lys Asp Leu
             220                 225

Val Lys Val Ile Gln Gln Glu Ser Tyr Thr Tyr Lys
     230                 235                 240

Asp Pro Ile Thr Glu Phe Val Glu Cys Leu Tyr Val
                 245                 250

Asn Phe Asp Phe Asp Gly Ala Gln Lys Lys Leu Arg
             255                 260

Glu Cys Glu Ser Val Leu Val Asn Asp Phe Leu
 265                 270                 275

Val Ala Cys Leu Glu Asp Phe Ile Glu Asn Ala Arg
             280                 285

Leu Phe Ile Phe Glu Thr Phe Cys Arg Ile His Gln
     290                 295                 300

Cys Ile Ser Ile Asn Met Leu Ala Asp Lys Leu Asn
                 305                 310

Met Thr Pro Glu Glu Ala Glu Arg Trp Ile Val Asn
                 315                 320

Leu Ile Arg Asn Ala Arg Leu Asp Ala Lys Ile Asp
 325                 330                 335

Ser Lys Leu Gly His Val Val Met Gly Asn Asn Ala
                 340                 345

Val Ser Pro Tyr Gln Gln Val Ile Glu Lys Thr Lys
     350                 355                 360

Ser Leu Ser Phe Arg Ser Gln Met Leu Ala Met Asn
                 365                 370

Ile Glu Lys Lys Leu Asn Gln Asn Ser Arg Ser Glu
     375                 380

Ala Pro Asn Trp Ala Thr Gln Asp Ser Gly Phe Tyr
 385                 390                 395
```

The present invention also discloses the nucleotide sequence of the human homologue of the Int6 cDNA where the human Int6 cDNA sequence is 89% homologous to the mouse sequence. Two overlapping recombinant clones (HINT6A and HINT6B) represent the 5' and 3' halves respectively of the human Int6 cDNA sequence. These two clones were deposited with the American Type Culture collection (ATCC), 12301 Parklawn Drive, Parkville, Md. 20852 on Jan. 24, 1995 and have ATCC accession numbers 97029 and 97030. The human Int6 cDNA sequence is shown below as SEQ ID NO:3.

```
ACTCCCTTTT CTTTGGCAAG ATGGCGGAGT ACGACTTGAC     40

TACTCGCATC GCGCACTTTT TGGATCGGCA TCTAGTCTTT     80

CCGCTTCTTG AATTTCTCTC TGTAAAGGAG ATATATAATG    120

AAAAGGAATT ATTACAAGGT AAATTGGACC TTCTTAGTGA    160

TACCAACATG GTAGACTTTG CTATGGATGT ATACAAAAAC    200

CTTTATTCTG ATGATATTCC TCATGCTTTG AGAGAGAAAA    240
```

-continued

```
GAACCACAGT GGTTGCACAA CTGAAACAGC TTCAGGCAGA      280

AACAGAACCA ATTGTGAAGA TGTTTGAAGA TCCAGAAACT      320

ACAAGGCAAA TGCAGTCAAC CAGGGATGGT AGGATGCTCT      360

TTGACTACCT GGCGGACAAG CATGGTTTTA GGCAGGAATA      400

TTTAGATACA CTCTACAGAT ATGCAAAATT CCAGTACGAA      440

TGTGGGAATT ACTCAGGAGC AGCAGAATAT CTTTATTTTT      480

TTAGAGTGCT GGTTCCAGCA ACAGATAGAA ATGCTTTAAG      520

TTCACTCTGG GGAAAGCTGG CCTCTGAAAT CTTAATGCAG      560

AATTGGGATG CAGCCATGGA AGACCTTACA CGGTTAAAAG      600

AGACCATAGA TAATAATTCT GTGAGTTCTC CACTTCAGTC      640

TCTTCAGCAG AGAACATGGC TCATTCACTG GTCTCTGTTT      680

GTTTTCTTCA ATCACCCCAA AGGTCGCGAT AATATTATTG      720

ACCTCTTCCT TTATCAGCCA CAATATCTTA ATGCAATTCA      760

GACAATGTGT CCACACATTC TTCGCTATTT GACTACAGCA      800

GTCATAACAA ACAAGGATGT TCGAAAACGT CGGCAGGTTC      840

TAAAAGATCT AGTTAAAGTT ATTCAACAGG AGTCTTACAC      880

ATATAAAGAC CCAATTACAG AATTTGTTGA ATGTTTATAT      920

GTTAACTTTG ACTTTGATGG GGCTCAGAAA AAGCTGAGGG      960

AATGTGAATC AGTGCTTGTG AATGACTTCT TCTTGGTGGC     1000

TTGTCTTGAG GATTTCATTG AAAATGCCCG TCTCTTCATA     1040

TTTGAGACTT TCTGTCGCAT CCACCAGTGT ATCAGCATTA     1080

ACATGTTGGC AGATAAATTG AACATGACTC CAGAAGAAGC     1120

TGAAAGGTGG ATTGTAAATT TGATTAGAAA TGCAAGACTG     1160

GATGCCAAGA TTGATTCTAA ATTAGGTCAT GTGGTTATGG     1200

GTAACAATGC AGTCTCACCC TATCAGCAAG TGATTGAAAA     1240

GACCAAAAGC CTTTCCTTTA GAAGCCAGAT GTTGGCCATG     1280

AATATTGAGA AGAAACTTAA TCAGAATAGC AGGTCAGAGG     1320

CTCCTAACTG GGCAACTCAA GATTCTGGCT TCTACTGAAG     1360

AACCATAAAG AAAAGATGAA AAAAAAAACT ATGAAAGAAA     1400

GATGAAATAA TAAAACTATT ATATAAAGGG TGACTTACAT     1440

TTTGGAAACA ACATATTACG TATAAATTTT GAAGAATTGG     1480

AATAAAATTG ATTCATTTTA                          1500
```

The deduced amino acid sequence of the human Int6 cDNA is shown below as SEQ ID NO:4 and starts at nucleotide 168 of SEQ ID NO:3 and extends 1188 nucleotides.

```
Met Val Asp Phe Ala Met Asp Val Tyr Lys Asn Leu
 1               5                  10

Tyr Ser Asp Asp Ile Pro His Ala Leu Arg Glu Lys
             15                  20

Arg Thr Thr Val Val Ala Gln Leu Lys Gln Leu Gln
 25                  30                  35

Ala Glu Thr Glu Pro Ile Val Lys Met Phe Glu Asp
             40                  45

Pro Glu Thr Thr Arg Gln Met Gln Ser Thr Arg Asp
         50                  55                  60

Gly Arg Met Leu Phe Asp Tyr Leu Ala Asp Lys His
                 65                  70

Gly Phe Arg Gln Glu Tyr Leu Asp Thr Leu Tyr Arg
         75                  80

Tyr Ala Lys Phe Gln Tyr Glu Cys Gly Asn Tyr Ser
 85                  90                  95

Gly Ala Ala Glu Tyr Leu Tyr Phe Phe Arg Val Leu
                100                 105

Val Pro Ala Thr Asp Arg Asn Ala Leu Ser Ser Leu
         110                 115                 120

Trp Gly Lys Leu Ala Ser Glu Ile Leu Met Gln Asn
                125                 130

Trp Asp Ala Ala Met Glu Asp Leu Thr Arg Leu Lys
         135                 140

Glu Thr Ile Asp Asn Asn Ser Val Ser Ser Pro Leu
145                 150                 155

Gln Ser Leu Gln Gln Arg Thr Trp Leu Ile His Trp
                160                 165

Ser Leu Phe Val Phe Asn His Pro Lys Gly Arg
                170                 175                 180

Asp Asn Ile Ile Asp Leu Phe Leu Tyr Gln Pro Gln
                185                 190

Tyr Leu Asn Ala Ile Gln Thr Met Cys Pro His Ile
                195                 200

Leu Arg Tyr Leu Thr Thr Ala Val Ile Thr Asn Lys
205                 210                 215

Asp Val Arg Lys Arg Arg Gln Val Leu Lys Asp Leu
                220                 225

Val Lys Val Ile Gln Gln Glu Ser Tyr Thr Tyr Lys
                230                 235                 240

Asp Pro Ile Thr Glu Phe Val Glu Cys Leu Tyr Val
                245                 250

Asn Phe Asp Phe Asp Gly Ala Gln Lys Lys Leu Arg
                255                 260

Glu Cys Glu Ser Val Leu Val Asn Asp Phe Leu
265                 270                 275

Val Ala Cys Leu Glu Asp Phe Ile Glu Asn Ala Arg
                280                 285

Leu Phe Ile Phe Glu Thr Phe Cys Arg Ile His Gln
                290                 295                 300

Cys Ile Ser Ile Asn Met Leu Ala Asp Lys Leu Asn
                305                 310

Met Thr Pro Glu Glu Ala Glu Arg Trp Ile Val Asn
                315                 320

Leu Ile Arg Asn Ala Arg Leu Asp Ala Lys Ile Asp
325                 330                 335

Ser Lys Leu Gly His Val Val Met Gly Asn Asn Ala
                340                 345
```

```
                           -continued
Val Ser Pro Tyr Gln Val Ile Glu Lys Thr Lys
    350             355                 360

Ser Leu Ser Phe Arg Ser Gln Met Leu Ala Met Asn
                365             370

Ile Glu Lys Lys Leu Asn Gln Asn Ser Arg Ser Glu
        375             380

Ala Pro Asn Trp Ala Thr Gln Asp Ser Gly Phe Tyr
385             390                 395
```

The amino acid sequence of human and mouse Int6 proteins are identical.

Variations are contemplated in the cDNA sequences shown in SEQ ID NOs:1 and 3 which will result in a DNA sequence that is capable of directing production of analogs of the proteins shown in SEQ ID NOs:2 and 4 respectively. It should be noted that the DNA sequences set forth above represents a preferred embodiment of the present invention. Due to the degeneracy of the genetic code, it is to be understood that numerous choices of nucleotides may be made that will lead to a DNA sequence capable of directing production of the instant Int6 proteins or their analogs. As such, DNA sequences which are functionally equivalent to the sequence set forth above or which are functionally equivalent to sequences that would direct production of analogs of the Int6 proteins produced pursuant to the amino acid sequences set forth above, are intended to be encompassed within the present invention.

The term analog includes any protein or polypeptide having an amino acid residue sequence substantially identical to a sequence specifically shown herein in which one or more amino acid residues have been conservatively substituted with a functionally similar residue. Examples of conservative substitutions include, for example, the substitution of one non-polar (i.e. hydrophobic) residue such as isoleucine, valine, leucine or methionine for another; the substitution of one polar (i.e. hydrophilic) residue for another, such as a substitution between arginine and lysine, between glutamine and asparagine, or between glycine and serine; the substitution of one basic residue such as lysine, arginine or histidine for another; or the substitution of one acidic residue, such as aspartic acid or glutamic acid for another.

The phrase conservative substitution may also include the use of a chemically derivatized residue in place of a non-derivatized residue.

Chemical derivative refers to an Int6 protein or polypeptide having one or more residues chemically derivatized by reaction of a functional side group. Examples of such derivatized molecules include, but are not limited to, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters, or other types of esters or hydrazides. Free hydroxyl groups may be derivatized to form O-acyl or O-alkyl derivatives. The imidazole nitrogen of histidine may be derivatized to form N-im-benzyllhistidine. Also included as chemical derivatives are those proteins or peptides which contain one or more naturally-occurring amino acid derivatives of the twenty standard amino acids. For example, 4-hydroxyproline may be substituted for proline; 5-hydroxylsine may be substituted for histidine; homoserine may be substituted for serine; and ornithine may be substituted for lysine.

The nucleic acid sequences provided by the present invention are useful as probes for a number of purposes. For example, they can be used as probes in Southern hybridization to genomic DNA and in the RNase protection method for detecting point mutations. The probes can be used to detect PCR amplification products. They may also be used to detect mismatches with the Int6 gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. The probes are complementary to Int6 gene coding sequences, although probes to introns are also contemplated. An entire battery of nucleic acid probes is used to compose a kit for detecting alteration of wild-type Int6 genes. The kit allows for hybridization to the entire Int6 gene. The probes may overlap with each other or be contiguous.

If a riboprobe is used to detect mismatches with mRNA, it is complementary to the mRNA of the human wild-type Int6 gene. The riboprobe thus is an anti-sense probe in that it does not code for the Int6 protein because it is of the opposite polarity to the sense strand. The riboprobe generally will be labeled with a radioactive, colorimetric, or fluorometric materials, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of Int6 gene. These allele-specific probes are useful to detect similar mutations in other patients on the basis of hybridization rather than mismatches. As mentioned above, the Int6 probes can also be used in Southern hybridizations to genomic DNA to detect gross chromosomal changes such as deletions and insertions. The probes can also be used to select cDNA clones of Int6 genes from tumor and normal tissues. In addition, the probes can be used to detect Int6 mRNA in tissues to determine if expression is altered as a result of mutation of wild-type Int6 genes. Provided with the Int6 gene and the Int6 cDNA sequences shown in SEQ ID NOs:1 and 3, design of particular probes is well within the skill of the ordinary artisan.

The present invention also relates to methods for detecting mutations of the Int6 gene in a subject.

For purposes of the present invention, subject means a mammal and mutation means inversion, translocation, insertion, deletion or point mutation of the wild-type Int6 gene.

It is believed that many mutations found in tumor tissues will be those leading to altered expression of Int6 protein. However, mutations leading to non-functional gene products can also lead to cancer. It is further understood that point mutations can occur in regulatory regions (e.g. promoter) or can disrupt proper RNA processing thus leading to reduced Int6 mRNA expression or loss of expression of the Int6 protein respectively.

The fact that integration of MMTV into the Int6 gene is observed in preneoplastic mouse mammary lesions suggests that mutations of Int6 are involved in early events of cancer. The methods of detecting mutations of the Int6 gene can therefore provide diagnostic and prognostic information. For example, detection of mutation of the Int6 gene in a tumor may effect the course of treatment chosen by a clinician. The methods of the present invention are applicable to any tumor in which mutations of Int6 occur. Loss of expression of the Int6 gene has been observed in tumors of the lung and breast. Thus, these are tumors in which Int6 has a role in tumorigenesis. In addition, since Int6 is expressed in all tissues tested including brain, heart, kidney, liver, ovaries, spleen and testes, mutations affecting the expression of the Int6 gene may contribute to neoplasia in these tissues too. Finally, since lung and breast tumors are derived from epithelial tissue, the methods of the invention may be useful in the detection of epithelial cell derived cancers such as nonsmall cell lung carcinomas.

It is further understood by one skilled in the art that the methods for detection disclosed in the present invention can be used prenatally to screen a fetus or presymptomatically to screen a subject at risk of having cancer based on his/her family history.

In one embodiment of the invention, the method for detecting mutations of the Int6 gene comprises analyzing the DNA of a subject for mutations of the wild-type Int6 gene. For analysis of DNA, a biological specimen is obtained from the subject. Examples of biological specimens that can be obtained for use in the present method, include, but are not limited to, tissue biopsies and blood. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. Alternatively, primary cell cultures can be established from tumor biopsies using methods known to those of ordinary skill in the art.

The DNA isolated from the biological specimen can be analyzed for mutations of the Int6 gene by a variety of methods including Southern blotting after digestion with the appropriate restriction enzymes (restriction fragment length polymorphism, RFLP) (Botstein, D. Amer. J. Hum. Genet. (1980) 69:201–205, denaturing gradient electrophoresis technique (Myers, R. M., Nature (1985) 313:495–498), oligonucleotide hybridization (Conner, R. et al., EMBO J. (1984) 3:13321–1326), RNase digestion of a duplex between a probe RNA and the target DNA (Winter, E. et al., Proc. Natl. Acad. Sci. U.S.A. (1985) 82:7575–7579), polymerase chain reaction (PCR) (Saiki, P. K. et al., Science (1988) 239:487–491; U.S. Pat. Nos. 4,683,195 and 4,683,202), ligase chain reaction (LCR) (European Patent Application Nos. 0,320,308 and 0,439,182), and PCR-single stranded conformation analysis (PCR-SSCP) (Orita, M. et al., Genomics (1989) 5:874–879; Dean, M. et al. Cell (1990) 61:863–871).

In one preferred embodiment, Southern blot analysis can be used to examine tumor or blood DNA for gross rearrangement of the Int6 gene. The DNA to be analyzed via Southern analysis is digested with one or more restriction enzymes. Following restriction digestion, resultant DNA fragments are separated by gel electrophoresis and the fragments are detected by hybridization with a labelled nucleic acid probe (Southern, E. M. J. Mol. Biol. (1975) 98:503–517).

The nucleic acid sequence used as a probe in Southern analysis can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) Proc. Natl. Acad. Sci., 70:2238–2242; Heck, R. F. 1968) S. Am. Chem. Soc., 90:5518–5523), methods which allow detection by chemiluminescence (Barton, S. K. et al. (1992) J. Am. Chem. Soc., 114:8736–8740) and methods utilizing biotinylated nucleic acid probes (Johnson, T. K. et al. (1983) Anal. Biochem., 133:126–131; Erickson, P. F. et al. (1982) J. of Immunology Methods, 51:241–249; Matthaei, F. S. et al. (1986) Anal. Biochem., 157:123–128) and methods which allow detection by fluorescence using commercially available products. The size of the probe can range from about 200 nucleotides to about several kilobases. A preferred probe size is about 500 to about 2000 nucleotides. The probe may be derived from introns or exons of the Int6 gene. Each of the nucleic acid sequences used as a probe in Southern analysis is substantially homologous to the corresponding portion of the murine or human Int6 genes where these genes have the cDNA sequences shown in SEQ ID NOs:1 or 3 respectively. In a preferred embodiment, the probes are derived from a human Int6 gene having the Int6 cDNA sequence shown in SEQ ID NO:3. By "substantially homologous" is meant a level of homology between the nucleic acid sequence used as a probe and the corresponding sequence of the human or murine Int6 genes. Preferably, the level of homology is in excess of 70%, most preferably in excess of 80%, with a particularly preferred nucleic acid sequence being in excess of 90% homologous with the sequence of the mouse or human Int6 genes.

Once the separated DNA fragments are hybridized to the labelled nucleic acid probes, the restriction digest pattern can be visualized by autoradiography and examined for the presence or absence of a restriction fragment length polymorphism (RFLP) associated with mutation of the Int6 gene.

In another preferred embodiment, genomic DNA may be analyzed for mutations in the Int6 gene via PCR-SSCP. In this method, each of the pair of primers selected for use in PCR are designed to hybridize with sequences in the Int6 gene to permit amplification and subsequent detection of mutations in the denatured amplification product via non-denaturing polyacrylamide gel electrophoresis. In a preferred embodiment, primer pairs are derived from the human Int6 gene. In a more preferred embodiment, primer pairs are derived from intronic sequences which border the 5' and 3' ends of a given exon of the human Int6 gene. Examples of primer pairs permitting specific amplification of the exons of the human Int6 gene include, but are not limited to,

| | |
|---|---|
| ACCAATAAAGTTTTAGTGAGCACAG | SEQ ID NO:5 |
| GCGCCCAAAGACCCCCTCAC | SEQ ID NO:6 |
| TTAATCAGTTTCTTTGGGGA | SEQ ID NO:7 |
| AGTTTCTAATGACAAAACTTAC | SEQ ID NO:8 |
| TCTTCTGCATTTTTAATTAG | SEQ ID NO:9 |
| CAAAATTAAGACGAGTTTAC | SEQ ID NO:10 |
| CTTATTTTGTTTCTGTGGCC | SEQ ID NO:11 |
| CATGACAACTTTAAAATATTTTT | SEQ ID NO:12 |
| AATTACAATGGGGTTTTAAA | SEQ ID NO:13 |
| GAAGAACCAAGGGAATCCTA | SEQ ID NO:14 |
| TTCAAGAGTATTCACAATAT | SEQ ID NO:15 |
| TGTGAAAAAGACGAACTCAC | SEQ ID NO:16 |
| AGTTTTCTTTATCTCACCCT | SEQ ID NO:17 |

```
                -continued
CAATATATATTTTAGTTTTAC       SEQ ID NO:18

CCGTTGACTTATTTTTACAG        SEQ ID NO:19

AAATAAAAATTCACACTTAC        SEQ ID NO:20

TTGTTGTATTTGTACATATAG       SEQ ID NO:21

ATCAAATCACGGTGTTCTTAC       SEQ ID NO:22

AAAACTAAGTTTTTAGGCCC        SEQ ID NO:23

ATAGCTAACATAATACTCAC        SEQ ID NO:24

TTCCCTGTGTTTCCTTTTAG        SEQ ID NO:25

ATAGAAGATGTGTGGTCTTAC       SEQ ID NO:26

GATTTCTTTTTGCATATTTTAG      SEQ ID NO:27

CAAGAAAACTGACAGCAAGA        SEQ ID NO:28
``` where SEQ ID NOs: 5 and 6 bound exon 1, SEQ ID NOs: 7 and 8 bound exon 2, SEQ ID NOs: 9 and 10 bound exon 3, SEQ ID NOs: 11 and 12 bound exon 4, SEQ ID NOs: 13 and 14 bound exon 5, SEQ ID NOs: 15 and 16 bound exon 6, SEQ ID NOs: 17 and 18 bound exon 8, SEQ ID NOs: 19 and 20 bound exon 9, SEQ ID NOs: 21 and 22 bound exon 10, SEQ ID NOs: 23 and 24 bound exon 11, SEQ ID NOs: 25 and 26 bound exon 12, and SEQ ID NOs: 27 and 28 bound exon 13. Optimization of the amplification reaction to obtain sufficiently specific hybridization to Int6 gene sequences is well within the skill in the art and is preferably achieved by adjusting the annealing temperature.

The primers of this invention can be synthesized using any of the known methods of oligonucleotide synthesis (e.g., the phosphodiester method of Agarwal et al. 1972. Agnew. Chem. Int. Ed. Engl. 11:451, the phosphotriester method of Hsiung et al. 1979. Nucleic Acids Res. 6:1371, or the automated diethylphosphoramidite method of Beuacage et al. 1981. Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In one embodiment, the primers can be derivatized to include a detectable label suitable for detecting and/or identifying the primer extension products (e.g., biotin, avidin, or radiolabeled dNTP's), or with a substance which aids in the isolation of the products of amplification (e.g. biotin or avidin).

In an alternative embodiment, primer pairs can be selected to hybridize to mutant forms of the Int6 disease gene. The selected primer pairs will hybridize sufficiently specifically to the mutated gene sequences such that non-specific hybridization to wild-type Int6 gene sequences will not prevent identification of the amplification product of the mutant gene sequence. Primer pairs which hybridize to mutations in the Int6 gene sequence can be used to amplify specific mutant gene sequences present in the DNA of a biological sample.

The amplification products of PCR can be detected either directly or indirectly. Direct detection of the amplification products is carried out via labelling of primer pairs. Labels suitable for labelling the primers of the present invention are known to one skilled in the art and include radioactive labels, biotin, avidin, enzymes and fluorescent molecules. The desired labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be analyzed for mutations of the Int6 gene via separating the PCR products by non-denaturing polyacrylamide gel electrophoresis, denaturing polyacrylamide gel electrophoresis (PCR-SSCP) or via direct sequencing of the PCR-products.

In yet another embodiment, unlabelled amplification products can be analyzed for mutations in the Int6 disease gene via hybridization with nucleic acid probes radioactively labelled or, labelled with biotin, in Southern blots or dot blots. Nucleic acid probes useful in the embodiment are those described earlier for Southern analysis. In yet another embodiment, detection of point mutations may be accomplished by molecular cloning of the allele present in the tumor tissue using the cDNA sequences set forth in SEQ ID NOs:1 and 3 and sequencing that allele using techniques well known in the art.

In a second embodiment, the method for detecting mutations of the Int6 gene comprises analyzing the RNA of a subject for alterations in Int6-specific mRNA expression.

For the analysis of RNA by this method, RNA can be isolated from blood or a tumor biopsy sample obtained from said subject where said tumors include, but are not limited to, tumors of the breast and lung.

The RNA to be analyzed can be isolated from blood or tumor biopsy samples as whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of whole cell RNA by acid-phenol (Chomczynski et al. 1987).

The methods for analyzing the RNA for alterations in the pattern or level of Int6-specific mRNA expression include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.), reverse-transcription polymerase chain reaction (RT-PCR) (Watson, J. D. et al. (1992) in "Recombinant DNA" Second Edition, W.H. Freeman and Company, New York) and RT-PCR-SSCP. One preferred method is Northern blotting.

The nucleic acid sequence used as a probe for detecting Int6-specific mRNA expression is substantially homologous to SEQ. ID. NOs. 1 or 3. By "substantially homologous" is meant a level of homology between the nucleic acid sequence and the cDNA sequence of SEQ ID NOs:1 or 3. Preferably, the level of homology is in excess of 70% more preferably in excess on 80%, with a particularly preferred nucleic acid sequence being in excess of 90% homologous with the cDNA sequence shown in SEQ ID Nos. 1 or 3.

In a second preferred embodiment, the RNA is analyzed for mutations in the Int6 gene by RT-PCR-SSCP. Single stranded cDNA is prepared from either tumor total RNA or polyA$^+$ enriched RNA using reverse transcriptase. In this method, each of the pairs of primers selected for use in PCR of the resultant single-stranded cDNA are designed to hybridize with sequences in the Int6 cDNA which are an appropriate distance apart (at least about 100–300 nucleotides) in the gene to permit amplification and subsequent detection of mutations in the denatured amplification product via non-denaturing polyacrylamide gel electrophoresis. Primer pairs which can specifically hybridize to overlapping Int6 gene sequences can be derived from the Int6 gene sequence. Primer pairs can be derived from the cDNA sequences set forth in SEQ ID NOs 1 and 3. In a preferred embodiment, the primers are derived from the human Int6 cDNA sequence shown in SEQ ID NO:3. Each primer of a pair is a single-stranded oligonucleotide of about 15 to about 20 bases in length which is complementary to a sequence at the 3' end of one of the strands of a double-stranded target sequence. Each pair comprises two such primers, one of which is complementary 3' end and the other of which is complementary to the other 3' end of the target sequence. The target sequence is generally about 100 to about 300 base pairs long. Optimization of the amplification reaction to obtain sufficiently specific hybridization to the Int6 cDNA is well within the skill in the art and is preferably achieved by adjusting the annealing temperature. Alternatively, the denatured RT-PCR products can be analyzed for mutations of the Int6 gene via direct sequencing of the RT-PCR products.

Yet another preferred method of analysis is the RNase protection method, which is described in detail in Winter et al., *Proc. Natl. Acad. Sci. USA*, 82: p. 7575, (1985) and Meyers et al., *Science*, 230: p 1242, (1985). In the practice of the present invention the method involves the use of a labeled riboprobe which is complementary to the human wild-type gene coding sequence. The riboprobe and either mRNA or DNA isolated from the tumor tissue are annealed (hybridized) together and subsequently digested with the enzyme RNase A which is able to detect mismatches in a duplex RNA structure. If a mismatch is detected by RNase A, it cleaves at the site of the mismatch. The riboprobe need not be the full length of the RNA or gene but can be a segment of either. If the riboprobe comprises only a segment of the Int6 RNA or Int6 gene it will be desirable to use a number of these probes to screen the whole mRNA sequence for mismatches.

The present invention also encompasses recombinant proteins derived from the cDNAs shown in SEQ ID Nos. 1 and 3. Recombinant Int6 proteins can be produced by recombinant DNA methodology known to one skilled in the art. Since the amino acid sequence of mouse (SEQ ID NO:2) and human (SEQ ID NO:4) Int6 proteins are identical, a suitable nucleic acid sequence capable of encoding a protein comprising all or part of the amino acid sequence shown in SEQ ID NO:4 is the sequence shown in SEQ ID NO:3 or in SEQ ID NO:1. In a preferred embodiment, such a suitable nucleic acid sequence can be cloned into a vector capable of being transferred into, and replicated in, a host organism.

The vectors contemplated for use in the present invention include any vectors into which a nucleic acid sequence as described above can be inserted along with any preferred or required operational elements, and which vector can then be subsequently transferred into a host organism and replicated in such organism. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the cloning vector of the present invention, it should additionally be noted that multiple copies of the nucleic acid sequence and its attendant operational elements may be inserted into each vector. In such an embodiment, the host organism would produce greater amounts per vector of the desired Int6 protein. The number of multiple copies of the DNA sequence which may be inserted into the vector is limited only by the ability of the resultant vector due to its size, to be transferred into and replicated and transcribed in an appropriate host microorganism.

In another embodiment, restriction digest fragments containing a coding sequence for Int6 protein can be inserted into a suitable expression vector that functions in prokaryotic or eukaryotic cells. By suitable is meant that the vector is capable of carrying and expressing a complete nucleic acid sequence coding for Int6 protein. Examples of expression vectors that function in prokaryotic cells such as bacteria include, but are not limited to, T7 promoter based vectors and vectors for producing trpE and lacZ fusions. Preferred expression vectors are those that function in a eukaryotic cell. Examples of such vectors include but are not limited to, vaccinia virus vectors, adenovirus, herpesviruses, baculovirus or mammalian type C retroviral vectors.

The selected recombinant expression vector may then be transfected into a suitable eukaryotic cell system for purposes of expressing the recombinant protein. Such eukaryotic cell systems include, but are not limited to cell lines such as human MCF10A or mouse HCll mammary epithelial cells. One preferred eukaryotic cell system for use with baculovirus vectors is SF21 ovarian cells from *spodoptera frugyerda*.

The expressed recombinant protein may be detected by methods known in the art which include Coomassie blue staining and Western blotting using sera containing anti-Int6 antibody.

In a further embodiment, the expressed recombinant protein can be obtained as a crude lysate or it can be purified by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the Int6 protein.

In yet another embodiment, the present invention relates to peptides derived from the Int6 amino acid sequences shown in SEQ ID Nos. 2 and 4 where those skilled in the art would be aware that the peptides of the present invention, or analogs thereof, can be synthesized by automated instruments sold by a variety of manufacturers, can be commercially custom ordered and prepared, or can be expressed from suitable expression vectors as described above. The term analog has been previously described in the specification and for purposes of describing peptides of the present invention, analogs can further include branched or non-linear peptides. Preferred peptides are those that range from about 20 to about 24 amino acids length and are immunogenic. As described in Example 8 herein, mutation of the Int6 gene can result in truncation of the expressed Int6 protein. Based on previous studies indicating that point-mutated ras proteins are processed in an appropriate manner to be targets for specific T cell-mediated cytotoxicity (Tsang; K. Y. et al. (1994) *Vaccine Research,* 3:183–193; Takahashi, H. S.; et al. (1989) *Science,* 246:118–121, Jung, S.; et al. (1991) *J. Exp. Med.,* 173:273–276, 1991; Peace, D. J.; et al. (1991) *J. Immunol.,* 146:2059–2065; Fenton, R. G.; et al. (1993) *J. Natl. Cancer Inst.,* 85:1294–1302; Gedde-Dahl, T., III; et al. (1992) *Hum. Immunol.,* 33:266–274, and Gedde-Dahl, T., III; et al. (1992) *Int. Immunol.,* 4:1331–1337), the mutated Int6 proteins may elicit a specific T-cell response via display on the tumor cell surface through the MHC apparatus.

The present invention therefore provides pharmaceutical compositions comprising Int6 protein or peptides derived therefrom for use in vaccines and in immunotherapy methods. When used as vaccines to protect mammals against cancer, the pharmaceutical composition can comprise as an immunogen cell lysate from cells transfected with a recombinant expression vector or a culture supernatant containing the expressed protein. Alternatively, the immunogen is a partially or substantially purified recombinant protein or a synthetic peptide.

The above compositions or formulations both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like. The immunogen may be administered once or at periodic intervals until a significant titer of anti-Int6 antibody is produced. The antibody may be detected in the serum using an immunoassay as described below.

In yet another embodiment, the present invention provides pharmaceutical compositions comprising nucleic acid sequence capable of directing host organism synthesis of an Int6 protein or of a peptide derived from the Int6 protein sequence. Such nucleic acid sequence may be inserted into a suitable expression vector by methods known to those skilled in the art. Expression vectors suitable for producing high efficiency gene transfer in vivo include, but are not limited to, retroviral, adenoviral and vaccinia viral vectors. Operational elements of such expression vectors are disclosed previously in the present specification and are known to one skilled in the art. Such expression vectors can be administered intravenously, intramuscularly, subcutaneously, intraperitoneally or orally.

Whether the immunogen is an Int6 protein, a peptide derived therefrom or a nucleic acid sequence capable of directing host organism synthesis of Int6 protein or peptides derived therefrom, the immunogen may be administered for either a prophylactic or therapeutic purpose. When provided prophylactically, the immunogen is provided in advance of the cancer or any symptom due to the cancer. The prophylactic administration of the immunogen serves to prevent or attenuate any subsequent onset of cancer. When provided therapeutically, the immunogen is provided at, or shortly after, the onset of cancer or any symptom associated with the cancer.

When the immunogen is a partially or substantially purified recombinant Int6 protein or an Int6 peptide, dosages effective to elicit an antibody response against Int6 range from about 10 µg to about 1500 µg.

Dosages of Int6 protein-encoding nucleic acid sequence effective to elicit an antibody response against Int6 range from about 10 to about 1000 µg.

The expression vectors containing a nucleic acid sequence capable of directing host organism synthesis of an Int6 protein(s) may be supplied in the form of a kit, alone, or in the form of a pharmaceutical composition as described above.

The present invention further relates to a vaccine for immunizing a mammal against cancer comprising Int6 protein or an expression vector capable of directing host organism synthesis of Int6 protein in a pharmaceutically acceptable carrier.

In addition to use as vaccines and in immunotherapy, the above compositions can be used to prepare antibodies to Int6 protein. To prepare antibodies, a host animal is immunized using the Int6 protein or peptides derived therefrom or aforementioned expression vectors capable of expressing Int6 protein or peptides derived therefrom. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80: 15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light chain genes in *E. coli* is the subject the PCT patent applications; publication number WO 901443, WO901443, and WO 9014424 and in Huse et al., 1989 Science 246:1275–1281.

Alternatively, anti-Int6 antibodies can be induced by administering anti-idiotype antibodies as immunogen. Conveniently, a purified anti-Int6 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the FC region of the administered antibodies can be removed. Following induction of anti-idiotype antibody in the host animal, serum or plasma is removed to provide an antibody composition. The composition can be purified as described above for anti-Int6 antibodies, or by affinity chromatography using anti-Int6 antibodies bound to the affinity matrix. The anti-idiotype antibodies produced are similar in conformation to the authentic Int6 antigen and may be used to prepare vaccine rather than using an Int protein.

When used as a means of inducing anti-Int6 antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

For both in vivo use of antibodies to Int6 proteins and anti-idiotype antibodies and for diagnostic use, it may be preferable to use monoclonal antibodies. Monoclonal anti-Int6 antibodies or anti-idiotype antibodies can be produced by methods known to those skilled in the art. (Goding, J. W. 1983. Monoclonal Antibodies: Principles and Practice, Pladermic Press, Inc., NY, N.Y., pp. 56–97). To produce a human-human hybridoma, a human lymphocyte donor is selected. A donor known to have the Int6 antigen may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal antibodies, the antibodies must bind to Int6 protein or peptide. For monoclonal anti-idiotype antibodies, the antibodies must bind to anti-Int6 antibodies. Cells producing antibodies of the desired specificity are selected.

The above described antibodies and antigen binding fragments thereof may be supplied in kit form alone, or as a pharmaceutical composition for in vivo use. When used as a pharmaceutical composition in immunotherapy, the antibodies or chimeric antibodies described herein may also be coupled to toxin molecules, radioisotopes, and drugs by conventional methods (Vitetta et al. (1991) in "Biologic Therapy of Cancer" De Vita V T, Hellman S., Rosenberg, S. A. (eds) J.B. Lippincott Co. Philadelphia; Larson, S. M. et al. (1991) in "Biological Therapy of Cancer" De Vita V. T., Hellman S., Rosenberg, S. A. (eds) J.B. Lippincott Co., Philadelphia). Examples of toxins to which the antibodies may be coupled to include, but are not limited to, Ricin and pseudomonas endotoxin. Examples of drugs or chemotherapeutic agents include, but are not limited to, adriamycin. Examples of radioisotopes, include, but are not limited to, $^{131}$I. Antibodies covalently conjugated to the aforementioned agents can be used in cancer immunotherapy. The antibodies may also be used as an immunoaffinity agent to purify Int6 proteins, for therapeutic uses, and for diagnostic use in immunoassays as described below.

The present invention therefore relates to a third method for detecting mutations of the Int6 gene comprising:

analyzing the protein of a subject for alterations in Int6 protein expression.

For analysis of protein by this method, protein is obtained from biological specimens such as tumor biopsy samples and the like. The protein can be obtained as a crude lysate or it can be further purified by methods known to one skilled in the art (Sambrook, J. et al. (1989) in "Molecular Cloning, A Laboratory Manual", Cold Spring Harbor press, Plainview, N.Y.).

Crude protein lysate can be analyzed for Int6 protein by immunoassays using anti-Int6 antibody.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Method in Immunodiagnosis,* 2nd Edition, Rose and Bigazzi, eds., John Wiley and Sons, 1980 and Campbell et al., *Methods of Immunology,* W.A. Benjamin, Inc., 1964, both of which are incorporated herein by reference. Such assays may be a direct, indirect, competitive, or noncompetitive immunoassay as described in the art. (Oellerich, M. 1984. *J. Clin. Chem. Clin.* BioChem. 22:895–904).

Detection of the Int6 protein anti-Int6 antibody complex formed can be accomplished by reaction of the complex with a secondary antibody such as labelled anti-rabbit antibody. The label may be an enzyme which is detected by incubating the complex in the presence of a suitable fluorimetric or colorimetric reagent. Other detectable labels may also be used, such as radiolabels, or colloidal gold, and the like. The labelled Int6 protein-anti-Int6 antibody complex is then visualized by autoradiography.

The present invention also includes a method for treating cancer comprising administering pharmaceutical compositions comprising an Int6 protein, an expression vector containing nucleic acid sequence capable of directing host organism synthesis of an Int6 protein, or anti-Int6 antibody in a therapeutically effective amount. When provided therapeutically, the Int6 protein, Int6 protein-encoding expression vector or anti-Int6 antibody coupled to radioisotopes, toxin molecules or drugs is provided at (or shortly after) the onset of infection or at the onset of any symptom of infection or disease caused by cancer. The therapeutic administration of the Int6 protein, Int6 protein-encoding expression vector, or anti-Int6 antibody serves to attenuate the infection or disease.

The present invention also includes another method for treating a subject having cancer comprising:

(a) immunizing a subject with an amount of Int6 protein or an expression vector capable of directing host organism synthesis of Int6 protein effective to elicit a specific T cell response;

(b) isolating said T cells from said immunized subject; and (c) administering said T cells to said immunized subject or to an unimmunized subject in a therapeutically effective amount.

T cells populations reactive against the Int6 protein may be isolated from a peripheral blood sample or spleen cells of a donor immunized with the Int6 protein. Epstein-Barr virus (EBV) can be used to immortalize human lymphocytes or a human fusion partner can be used to produce human-human hybridomas. Primary in vitro immunization with Int6 protein can also be used in the generation of T cells reactive to the Int6 protein.

T cells are cultured for about 7 to about 90 days (Yanelli, J. R. J. Immunol. Methods 139:1–16 (1991)) and then screened to determine the clones of the desired reactivity against the other peptide contained in the immunogenic chimeric protein using known methods of assaying T cell reactivity; T cells producing the desired reactivity are thus selected.

The above described T cells may be used for in vivo use as treatment for individuals afflicted with cancer by administering T cells to a mammal intravenously, intraperitoneally, intramuscularly or subcutaneously. Preferred routes of administration are intravenously or intraperitoneally.

The present invention also relates to a gene therapy method in which an expression vector containing a nucleic acid sequence representing the wild-type Int6 gene is administered to a subject having a mutation of the Int6 gene. A nucleic acid sequence representing wild-type Int6 gene is that shown in SEQ ID No. 1 and SEQ ID No:3. Such nucleic acid sequence may be inserted into a suitable expression vector by methods known to those skilled in the art. Expression vectors suitable for producing high efficiency gene transfer in vivo include retroviral, adenoviral and vaccinia viral vectors.

Expression vectors containing a nucleic acid sequence representing wild-type Int6 gene can be administered intravenously, intramuscularly, subcutaneously, intraperitoneally or orally. A preferred route of administration is intravenously.

The invention also provides a diagnostic kit for detecting mutations of the Int6 gene. This diagnostic kit comprises purified and isolated nucleic acid sequences useful as PCR primers in analyzing DNA or RNA for mutations of the Int6 disease gene.

Any articles or patents referenced herein are incorporated by reference. The following examples are presented to illustrate various aspects of the invention but are in no way intended to limit the scope thereof.

EXAMPLES

Example 1

Identification of a Novel Integration Site for the MMTV Genome

Figure 1B:
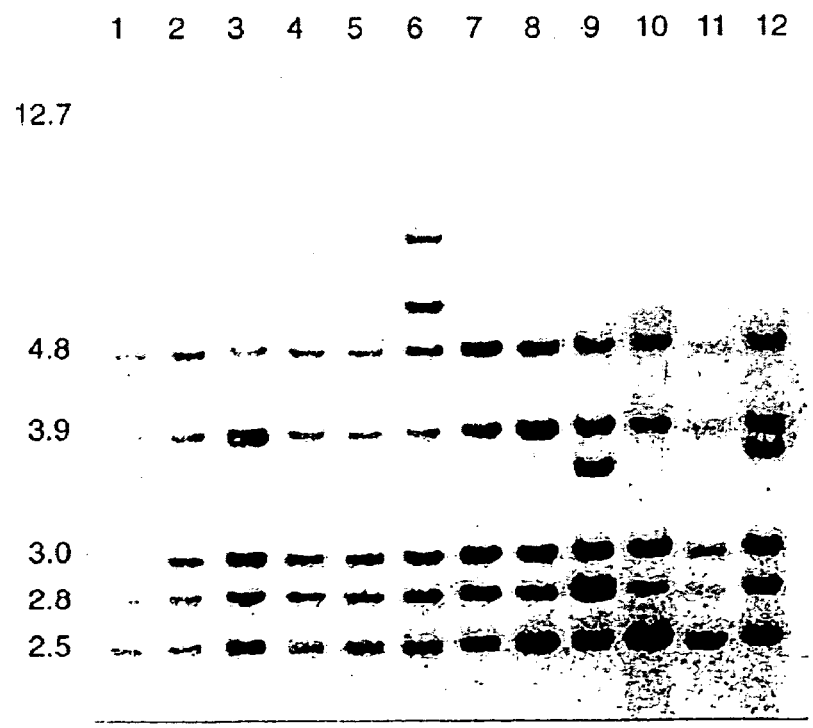

To identify new Int loci in mammary tumor DNAs that would not be biased by selective inbreeding for a high cancer phenotype, a feral mouse strain derived from a single breeding pair of *M. musculus* trapped in Czechoslovakia (CZECH II) (Gallahan, D. and Callahan, R. (1987) *J. Virol,* 61:66–74) was utilized. The CZECH II mice, unlike high-incidence inbred mouse strains, lack endogenous MMTV genomes but do contain an infectious strain of MMTV that is transmitted congenitally through the milk (Callahan, R. et al. (1982) *Proc. Natl. Acad. Sci. U.S.A.,* 79:4113–4117). In the CZECH II mice, several preneoplastic hyperplastic outgrowth lines (HOGs) were developed which are stable, clonal-dominant and develop focal mammary tumors which sometimes metastasis to the lung. In order to detect the integration of MMTV proviral genome into genomic DNA of the HOGs or HOG-derived tumor or lung metastasis from a mouse having a HOG-derived tumor, cellular DNA was isolated from a CZECH II HOG line designated CZZ1 or from CZZ-1 derived malignant tumors or lung metastasis and analyzed by Southern blotting as follows. 10 ug of cellular DNA was digested by EcoRI, run on a 0.8% agarose gel, transferred to a nylon membrane and hybridized with MMTV LTR probe as described in Gallahan, D. and Callahan R. (*J. Virol* (1987) 61:66–74. In Brief, before hybridization, filters were soaked for 4 to 24 hours at 37° C. in a prehybridization solution containing 3×SSPE (1×SSPE is 180 mM NaCl, 10 mM $NaH_2PO_4$ [pH 7.4], and 1 mM EDTA), 5×Denhardt solution (0.02% Ficoll, 0.02% polyvinylpyrrolidone, 0.02% bovine serum albumin), 2.5% dextran sulfate, and 50% formamide. Denatured probe was added to a solution similar to the prehybridization solution except that it contained 40% formamide. The mixture was added to the plastic bag containing prehybridized filters and incubated at 37° C. for 24 h. The filters were washed in stringent conditions involving three changes (each change done after 20 to 30 minutes of washing) of 0.1×SSC (1×SSC is 0.15 M NaCl plus 0.015 M sodium citrate) and 0.5% sodium dodecyl sulfate at 65° C. The filters were exposed to Kodak XAR-5 C-ray film overnight or for up to several days. The results of these Southern blots are shown in FIGS. 1A and 1B. The results presented in FIG. 1A show that DNA from one CZZ-1 HOG line contained three MMTV proviral genomes (six EcoRI restriction fragments) integrated into the cellular DNA and that these proviral genomes were also present in primary tumors which arose independently from within the HOG. The results further demonstrated that CZZ-1 was clonal-dominant population of preneoplastic cells because these six MMTV-related fragments were reproducibly found in the original outgrowth and in each succeeding transplant generation. Indeed, the clonal-dominant nature of the CZZ-1 HOG is illustrated by tumor 1262 (lane 3, FIG. 1A) in which one complete proviral genome, corresponding to the 4.8 and 2.8 Kb EcoRI restriction fragments, has been lost. The observation that five out of the thirteen tumor DNAs analyzed in FIG. 1A and five out of eleven independent metastatic lesions in the lung of the mouse bearing tumor 4973 (FIG. 1B) contained additional integrated MMTV genomes suggested that the additional integration events may have contributed to tumor progression by activating (or inactivating) additional cellular genes. However, since none of the known common insertions sites (Wnt-1, Fgf-3, Int-3, Wnt-3, and Fgf-4) were rearranged by MMTV in the CZZ-1 HOG, recombinant clones were obtained for each of the EcoRI host-MMTV junction restriction fragments in the CZZ-1 HOG and subclones of the host sequences were used as probes to screen Southern blots of independent MMTV-induced mammary tumor DNAs for evidence of MMTV-induced DNA rearrangements.

Figure 2A:
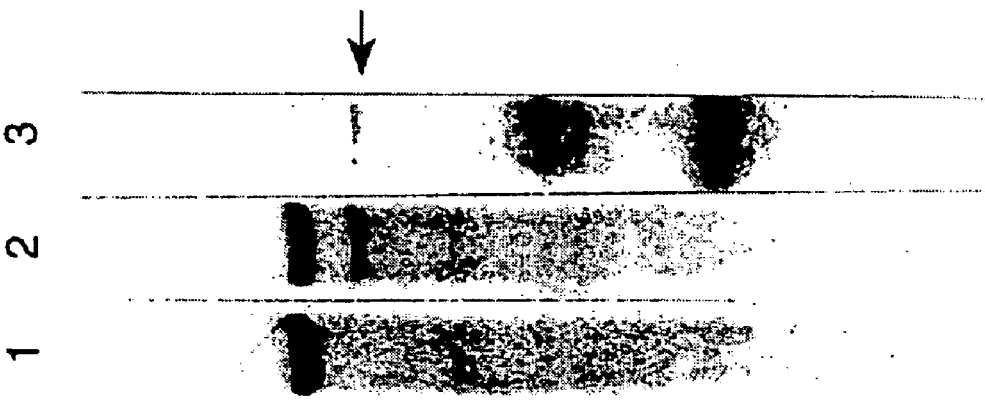
FIGS. 2A–2C show the results of Southern blot analyses of 10 micrograms of cellular DNA digested with EcoRI, separated by agarose gel electrophoresis and hybridized as follows. Lanes 1 and 2 of the blots in FIGS. 2A and 2B were hybridized with probe D which corresponds to host flanking sequences. Lane 2 of the blots in FIGS. 2A and 2B was subsequently hybridized with MMTV gag sequences (a 2.0 kb-Pst-XhoI fragment from MMTV GR-40; Gallahan and Callahan *J. Virol*, 61, 66–74: (1987)) and the results are shown in lane 3 in FIGS. 2A and 2B. Lanes 1 and 2 in FIG. 2C were hybridized with probe C. Lane 2 was subsequently hybridized with MMTV env sequences (1.7 kb PstI fragment from MMTV (C3H); Gallahan and Callahan *J. Virol*, 61: 66–74; (1987)) and the result is shown in lane 3 in FIG. 2C. The DNAs analyzed were isolated from CZZ-1 HOG derived tumor 22 (FIG. 2A, lanes 2 and 3), independent mammary tumor 1139 (FIG. 2B, lanes 2 and 3) independent mammary tumor 3134 (FIG. 2C, lanes 2 and 3), and normal liver. (Lane 1 in FIGS. 2A–2C). The presence of the arrow in FIGS. 2A–2C indicates the site of the MMTV induced rearranged restriction fragment. The locations of probes C and D in the Int6 gene are shown in FIG. 3.
Figure 2B:
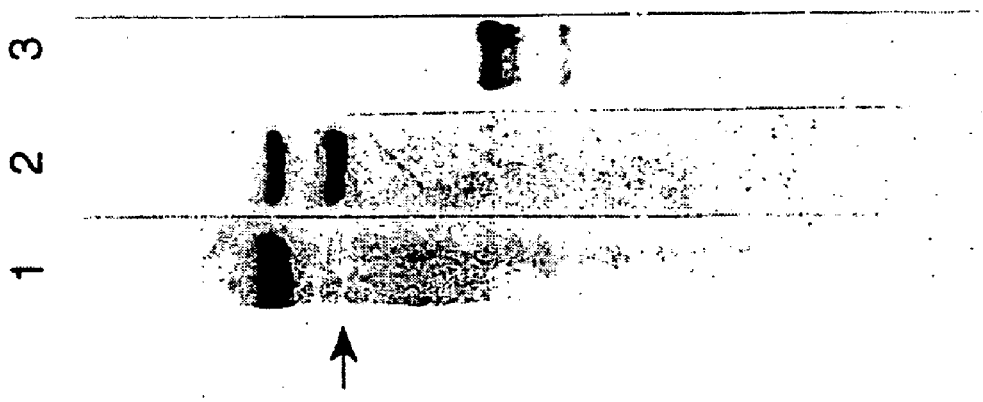
Figure 2C:
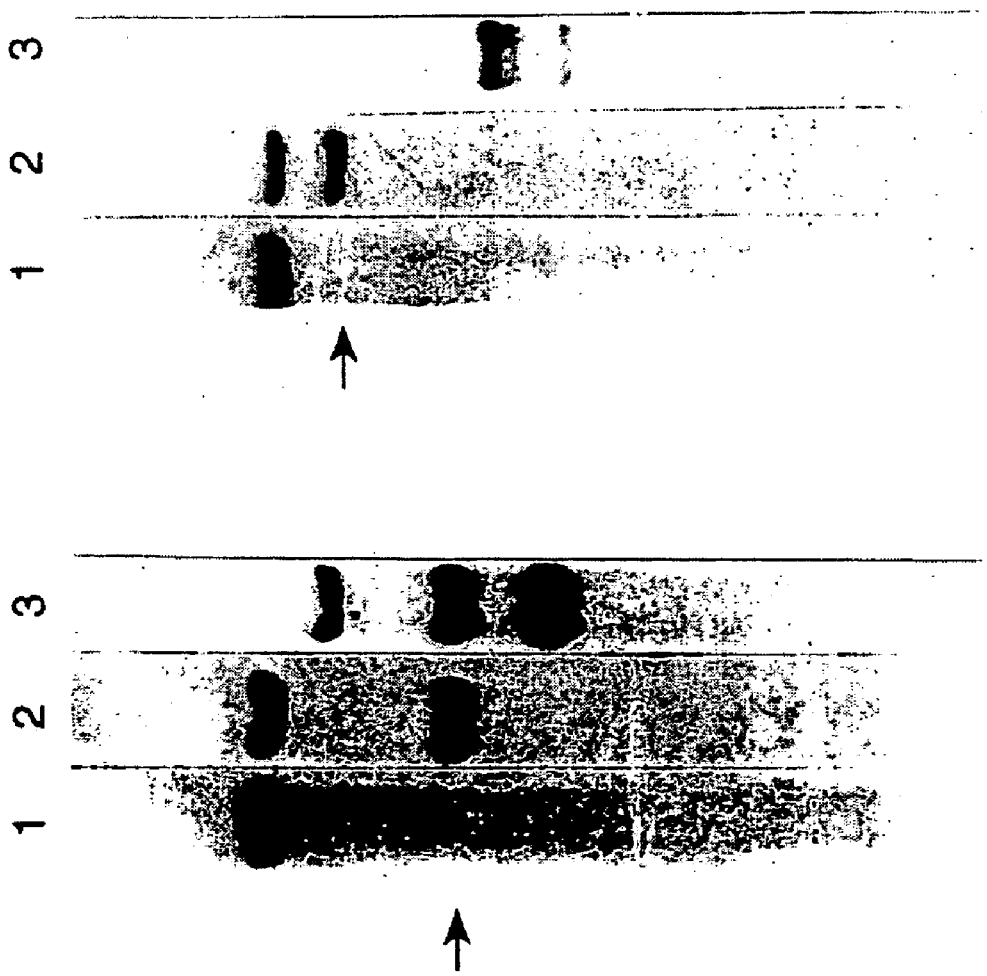

Using this approach, a probe consisting of the host sequences flanking one of the MMTV proviruses in the CZZ-1 HOG (i.e., the 3.0 Kb fragment shown in FIG. 1A) was used to identify an Int6 common integration site in the CZZ-1 HOG derived tumor 22 (FIG. 2A, lanes 2 and 3) and independent mammary tumors 1139 (FIG. 2B, lanes 2 and 3) and 3144 (FIG. 2C, lanes 2 and 3). In brief, cellular DNAs (10 µg) from each tumor DNA and from normal liver DNA (lane 1 in each panel) were digested with EcoRI, run on a 0.8% agarose gel, and then blotted onto a nylon membrane. Lanes 1 and 2 of the blots in FIGS. 2A and 2B were hybridized with probe D which corresponds to host flanking sequences. Lane 2 of FIGS. 2A and 2B was subsequently hybridized with MMTV gag sequences (Gallahan and Callahan (1987) *J. Virol,* 61:66–74) and the results are shown in lane 3 of FIGS. 2A and 2B. Lanes 1 and 2 in FIG. 2C were hybridized with probe C. Lane 2 was subsequently hybridized with MMTV env sequences (Gallahan and Callahan (1987) *J. Virol,* 61:66–74) and the result is shown in lane 3 of FIG. 2C. Hybridizations of the respective blots with the first probe were carried out as described earlier in this Example (Gallahan and Callahan ((1987) *J. Virol.* 61:66–74). Where blots were subsequently hybridized with a second probe, the blots were reprobed according to Gallahan and Callahan ((1987) *J. Virol.,* 61:66–74) as follows. In brief, Genetran filters were stripped of probe DNA by placing the filters in 100 ml of 0.4 N NaOH and incubated for 20 minutes at room temperature. This solution was then discarded and replaced with 0.1 M Tris (pH 7.5)-0.1×SSC-0.5% sodium dodecyl sulfate solution to neutralize the filter. The filter was incubated for 15 minutes at room temperature, after which the neutralization solution was replaced and incubation was continued for another 15 minutes. The filter was then prehybridized and hybridized as described earlier in this Example. Genetran filters treated in this way could be re-used at least five times before noticeable. DNA loss.

The results show that MMTV-induced rearrangements (indicated by an arrow in FIGS. 2A–2C) were detected in the two independent MMTV-induced mammary tumor DNAs (lanes 2 and 3 of FIGS. 2B and 2C) Of interest, in each case where MMTV-induced rearrangements were detected, the rearranged restriction fragment co-migrated with a fragment containing either MMTV gag or env sequences. These results demonstrate that the transcriptional orientation of the viral genome in each tumor was in the same direction. Thus, the host sequences adjacent to the integrated MMTV genome define a new common integration site from MMTV designated Int6.

Example 2

Isolation of the Murine Int6 Gene

Figure 3:
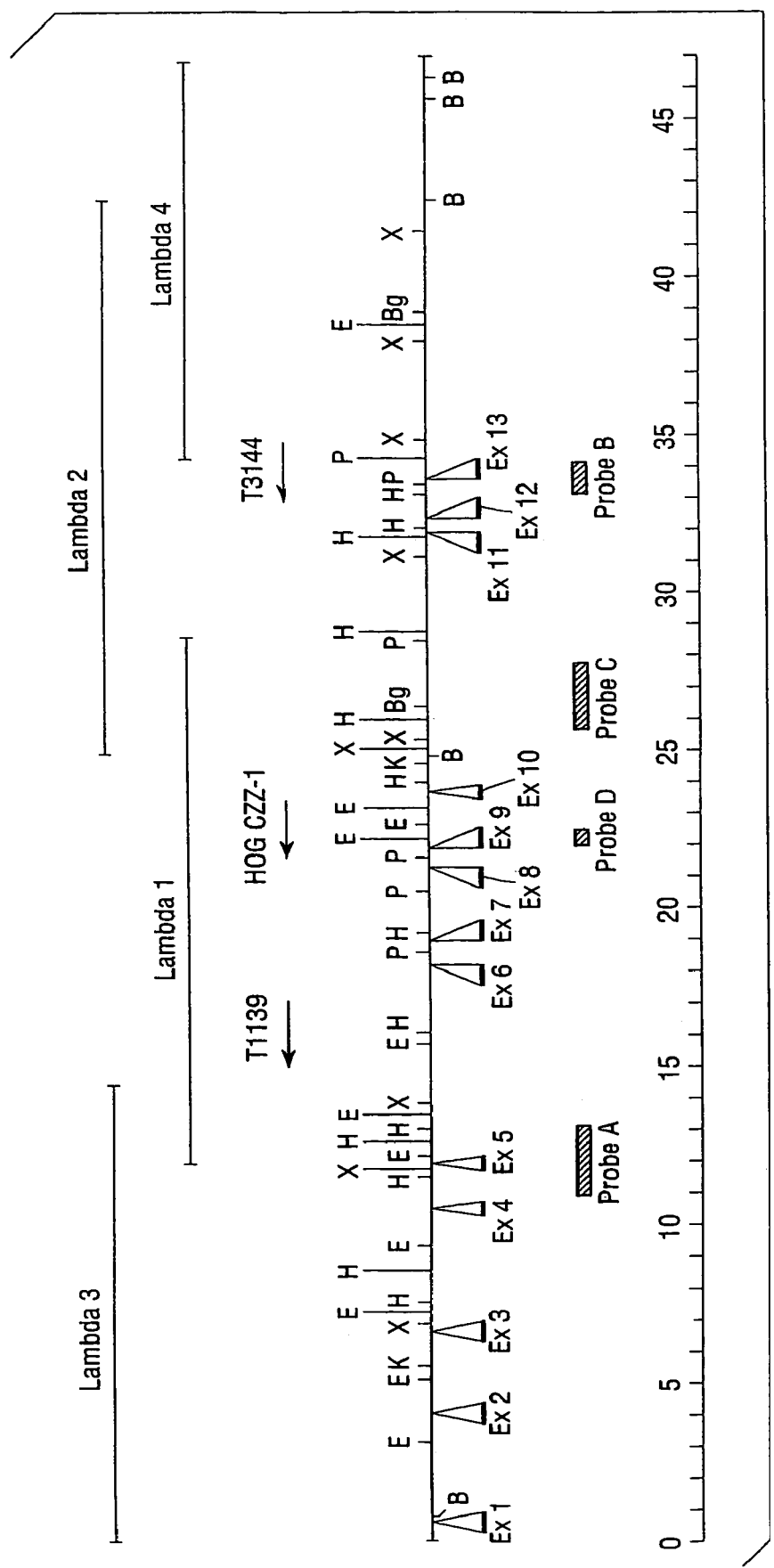
FIG. 3 is a schematic diagram of the murine Int6 locus in which the location of the four overlapping lambda clones which span the Int6 locus (designated 1 to 4) are shown relative to a partial restriction map of sites for EcoRI (E), XbaI (X), PstI (P), BglII (BGL), HindIII (H), and BamHI (B) in the Int6 locus. The location of the Int6 exons and of restriction fragments used as probes A–D are indicated below the restriction map by solid and hatched boxes respectively. The scale of the restriction map is given in increments of 1.0 kb at the bottom of the Figure while the location and transcriptional orientation of integrated MMTV proviral genomes within the Int6 gene of tumors 1139 and 3144, or within the Int6 gene of the CZZ-1 HOG, is indicated by arrowheads above the restriction map.

To obtain recombinant genomic clones of the Int6 loci, a subclone of the 3.0 kb EcoRI fragment (shown in FIG. 1A) containing the host flanking sequences (i.e. probe D, FIG. 3) was used to probe a lambda phage library (Stratagene, LaJolla, Calif.) of genomic DNA from mouse strain 129/sv. This genomic DNA contains wild-type Int6 DNA as determined by nucleotide sequence analysis. An additional three overlapping lambda clones which span 47 kb of the Int6 locus have also been obtained using probes A–C (FIG. 3). Together, these four overlapping lambda clones span the murine Int6 gene as shown in FIG. 3. The gene is located centromeric of the myc proto-oncogene on mouse chromosome 15. Further nucleotide sequence analysis of the genomic clones of the Int6 locus demonstrated that the gene contains thirteen exons which span 34 Kb of genomic DNA as shown in FIG. 3.

Example 3

Expression of the Int6 Gene in CZECH II Mammary Tumors

Figure 4:
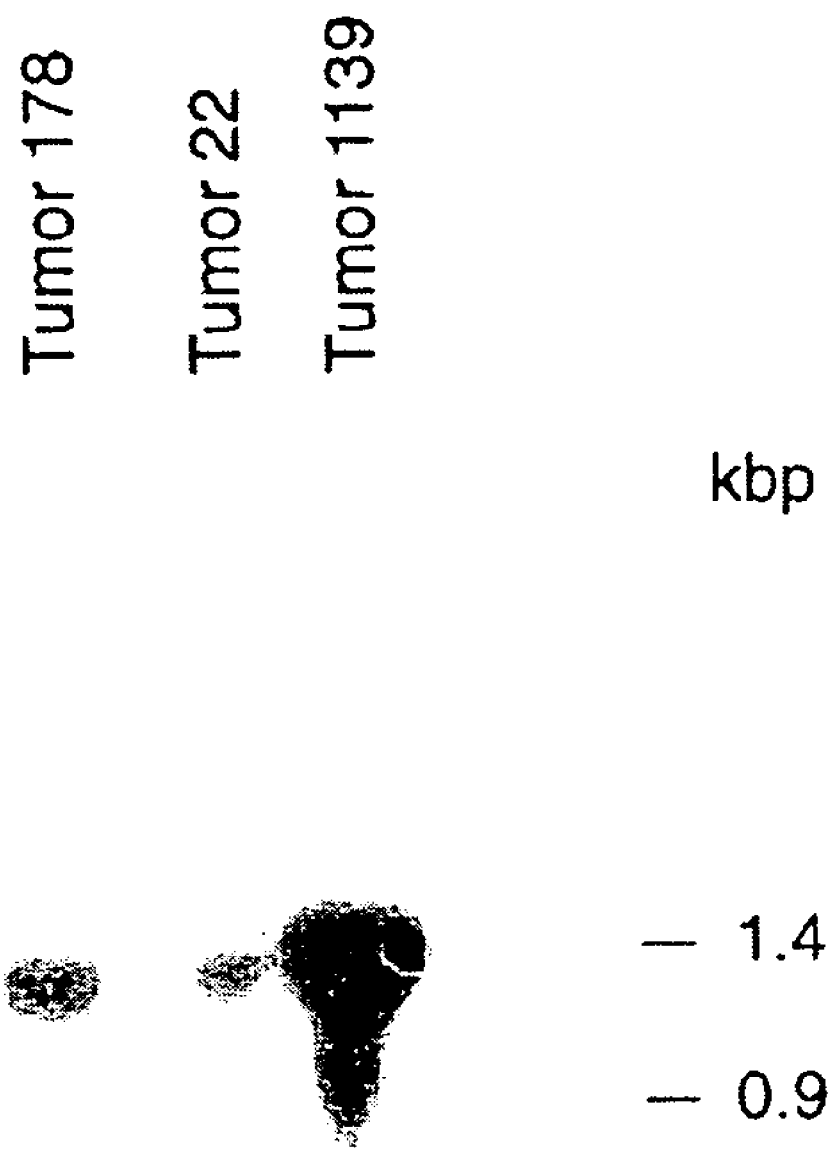
FIG. 4 shows the results of Northern blot analysis of total RNA isolated from Int6 negative tumor (tumor 178) and the Int6 positive tumors (22 and 1139). The RNAs were denatured in the presence of formaldehyde, separated on a 1% agarose gel containing formaldehyde, and hybridized with probe A.

To examine Int6 expression in CZECH II mammary tumors, total RNA (20 µg) prepared from the Int6 negative tumor (tumor 178) and from Int6 positive tumors having viral insertions in Int6 (22 and 1139) was denatured in the presence of formaldehyde and run on a 1% agarose gel containing formaldehyde. The RNA was then transferred to a nylon membrane and hybridized with probe A (FIG. 3) as described in Gallahan, D. and Callahan, R. (1987) *J. Virol.,* 61:66–74. The results of the Northern blots are shown in FIG. 4. In brief, hybridization with probe A detected a 1.4 Kb species of RNA in each of three tumors and tumor 1139 also contained a 0.9 Kb species of RNA related to sequences in probe A. The observation that tumor 178 (FIG. 4) and several other MMTV induced mammary tumors in which Int6 is not rearranged by the virus expressed the 1.4 kb RNA species detected by probe A. This suggests that in tumors 22 and 1139 the level of the Int6 gene expression is not an important consequence of viral integration in this locus.

Example 4

Isolation of Wild-Type Murine Int6 cDNA

In order to isolate a cDNA corresponding to wild-type 1.4 kb Int6 RNA, a murine cDNA library of an MMTV induced mammary tumor in which Int6 was not rearranged by MMTV was prepared using standard techniques (Sambrook et al (1989) in "Molecular Cloning, A Laboratory Manual", Cold Spring Harbor Press, Plainview N.Y.) and was probed with probe A (probe A is the XbaI fragment shown in FIG. 3). The nucleotide sequence of the murine Int6 cDNA was determined and is shown in FIG. 5. Translation of the 1.4 kb species of Int6 RNA revealed an open reading frame which encodes a 43.5 kilodalton protein. As shown in FIG. 5, this protein contains two potential N-glycosylation site motifs (Gavel, Y. and von Heijne, G. (1990) *Protein Eng.,* 3:433–442) as well as potential phosphorylation site motifs for cyclic AMP/cyclic GMP-dependent protein kinase (Glass, D. B. et al (1986) *J. Biol. Chem.,* 261:2987–2993), protein kinase C (Kishimoto, A. et al (1985) *J. Biol. Chem.,* 260:12492–12499), tyrosine kinases (Hunter, T. and Cooper, J. A. (1985) *Ann. Rev. Biochem,* 54:897–930) and casein kinase II (Pinna, L. A. (1990) *Biochim Biophys Acta,* 1054: 267–284).

Example 5

Conservation of the Int6 cDNA Across Species

Figure 6:
FIG. 6 shows the results of a "Zoo" blot in which cellular DNA (10 μg each) isolated from *C. Elegans, Drosophila, Xenopus,* chicken, mouse and human was hybridized with Int6 cDNA under high stringency conditions.

Since all of the genes whose expression has been affected or altered by MMTV integration in mouse mammary tumors have been highly conserved through evolution (Dickson, C. and Peters, G. (1987) *Nature* 326:883; Rijsewizk, K. F. et al (1987) *Cell,* 50:649–657; Robbins, J. et al (1992) *J. Virol.,* 66:2594–2599), the conservation of the Int6 gene in genomic DNA of different species was examined via Southern blot analysis. Cellular DNAs (10 µg each) from *C. elegans, Drosophila,* Xenopus, chicken, mouse, and human were digested with BamHI, run on a 0.8% agarose gel, transferred to a nylon membrane and hybridized overnite with Int6 cDNA in 3×SSPE (1×SSPE is 180 mM BaCl, 10 mMNaH$_2$PO$_4$ (pH 7.4, and 1 mM EDTA), 5×Denhardt solution (0.02% Ficoll, 0.02% polyvinylpyrrolidone, 0.02% bovine serum albumin), 5% dextran sulfate and 2% SDS (sodium dodecyl sulfate) at 65° C. After hybridization, the blot was washed in stringent condition involving three changes (each change done after 20 to 30 minutes of washing) 0.5×SSC (1×SSC is 0.15 M NaCl plus 0.015 M sodium citrate) plus 0.5% SDS at 65° C. Exposure to Kodak XAR-5 film was for three days. As shown in FIG. 6, Int6 related sequences can be detected in all the eukaryotic species examined. Restriction fragments of yeast DNA which contain Int6 related sequences were also detected by Southern blot analysis (data not shown).

In addition, the nucleotide sequence of a cDNA clone of the *Drosophila* homolog of Int6 has been determined (data not shown) and the deduced amino acid sequence of the *Drosophila* Int6 protein is 60% identical to the human/mouse deduced amino acid sequences. Taken together, these results demonstrate an extensive evolutionary conservation of the Int6 gene which is indicative of Int6 serving a basic life function.

Example 6

Detection of Int6-specific mRNA Expression in Target Tissues

Figure 7A:
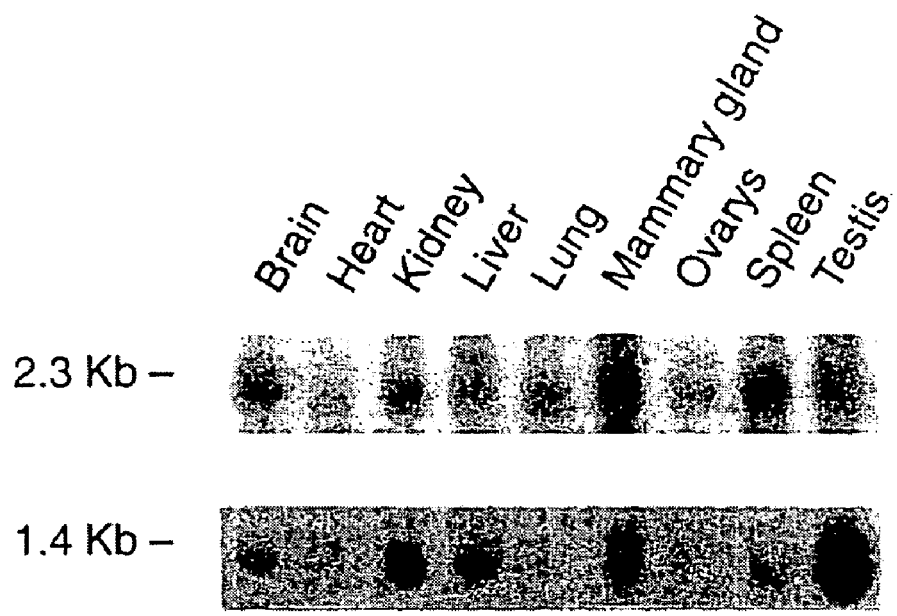
FIG. 7 shows the results of Northern blot analyses of total RNA (10 μg each) isolated from normal adult tissues (top panel) and from developing embryos (lower panel). The RNAs were denatured in the presence of formaldehyde, run on 1% agarose gels containing formaldehyde and then transferred to a nylon membrane and hybridized sequentially with a β-actin-probe (the 2.3 kb mRNAs) and then a murine Int6 cDNA probe (the 1.4 kb mRNAs).
Figure 7B:
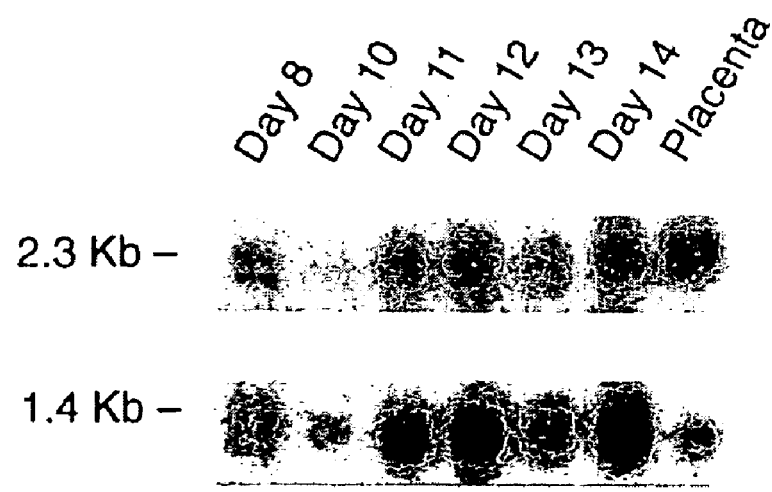

Having detected the 1.4 Kb Int6 RNA species in a tumor in which the gene was not rearranged by MMTV (i.e., tumor 178, FIG. 4) normal adult tissues and embryos at different stages of development were surveyed for Int6 RNA expression via Northern analysis as follows. Total RNAs (10 µg each) was prepared from the indicated tissues. The RNAs were denatured in the presence of formaldehyde and run on 1% agarose gels containing formaldehyde. The RNA samples were then transferred to a nylon membrane and hybridized sequentially with a β-actin probe and then an Int6 cDNA probe under conditions described in Gallahan and Callahan (*J. Virol.,* 61:66–74 (1987)). As shown in FIG. 7, Int6 RNA is expressed in all adult tissues tested, including the mammary gland, and expression of Int6 RNA in embryos was detected as early as day eight of development.

Example 7

Detection of Int6-specific mRNA Expression in Target Tissues

To detect Int6-specific mRNA expression, Random primed cDNA is prepared using total RNA from the various tissues. A 700 bp fragment of Int6 murine cDNA is amplified by PCR using the primers shown as SEQ ID NO. 29 TGTCCACATATTCTACGCTA and SEQ ID NO. 30 TGTATGTCATCCTTTATACA. The conditions of the PCR are: 30 cycles of denaturation at 94° C. for 1 minute, annealing at 55° C. for 1 minute, and extension at 72° C. for 2 minutes. After the last cycle there is an additional extension time of 2 minutes. The PCR product is run on a 1.0% agarose gel. The RT-PCR products are detected by photographing the gel following staining with ethidium bromide.

Example 8

Rearrangement of Int6 by MMTV Leads to the Expression of Novel Species of Int6 RNA in Mammary Tumors Inspection of the mapping data for the murine Int6 gene as shown in FIG. 3 reveals that all of the viral integration events occur within introns of the Int6 gene and that the transcriptional direction of the integrated viral genome is in the opposite orientation to that of the Int6 gene. There are at least four possible scenarios for the role MMTV plays at the Into locus. In the first, the Int6 gene is in fact not the target gene on which MMTV acts. At the Wntl, Fgf-3, and Fgf-4 loci (Dickson, C., et al. (1984) Cell. 37:529–536; Nusse, R., et al. (1982) Cell. 31:99–109; Peters, G., et al. (1989) Proc. Natl. Acad. Sci. USA. 86:5678–5682), MMTV integration sites cluster around the target gene in an ordered fashion and the transcriptional orientation of the integrated viral genomes 5' of the target gene are in the opposite direction to that of the target gene whereas those 3' of the target gene are in the same transcriptional orientation. Further, based on published reports, MMTV integration sites are within 15 kb of the particular target gene. However, since no evidence was found for the activation of expression of RNA corresponding to sequences up to 13 kb 3' of the Int6 gene, the location of the putative target gene would have to be more than 24 kb from the integrated MMTV genome in CZZ-1 HOG and more than 30 kb in tumor 1139 (see FIG. 3), thereby making this possibility much less likely.

A second possible consequence of MMTV integration into the Int6 gene is the activation of expression of a new chimeric RNA transcript of Int6 initiated by the 3' LTR of the integrated viral genome. An analogous situation occurs in MMTV-induced rearrangements of Int-3 (Robbins, J., et al. (1992) J. Virol., 66:2594–2599) except in the case of Int6, this would result in the expression of Int6 anti-sense RNA since the transcriptional orientation of the viral genome is opposite to that of Int6. Such a result would represent a trans-dominant mutation that would inactivate the expression of both alleles. However, using a variety of techniques, MMTV-induced Int6 antisense RNA expression has not been detected.

A third possibility assumes that the Int6 gene is the target for MMTV integration within the Int6 locus. In this case the viral insertion would disrupt the expression of one allele and reveal the presence of a spontaneous recessive mutation in the other allele. To examine this possibility the nucleotide sequence of cDNA corresponding to the non-rearranged allele of Int6 in tumor 22 and tumor 1139 was determined and in both cases no mutation was found.

The fourth and more plausible scenario is that MMTV integration into the Int6 gene causes the expression of a biologically activated gene product (like Int3, (Robbins, J., et al. (1992) J. Virol., 66:2594–2599)) or a dominant-negative gene product either of which deregulates the normal control of mammary epithelial cellular growth leading to hyperplasia of the affected mammary epithelial cells. This would create a premalignant epithelial cell population with which mammary tumors could subsequently develop.

Figure 8:
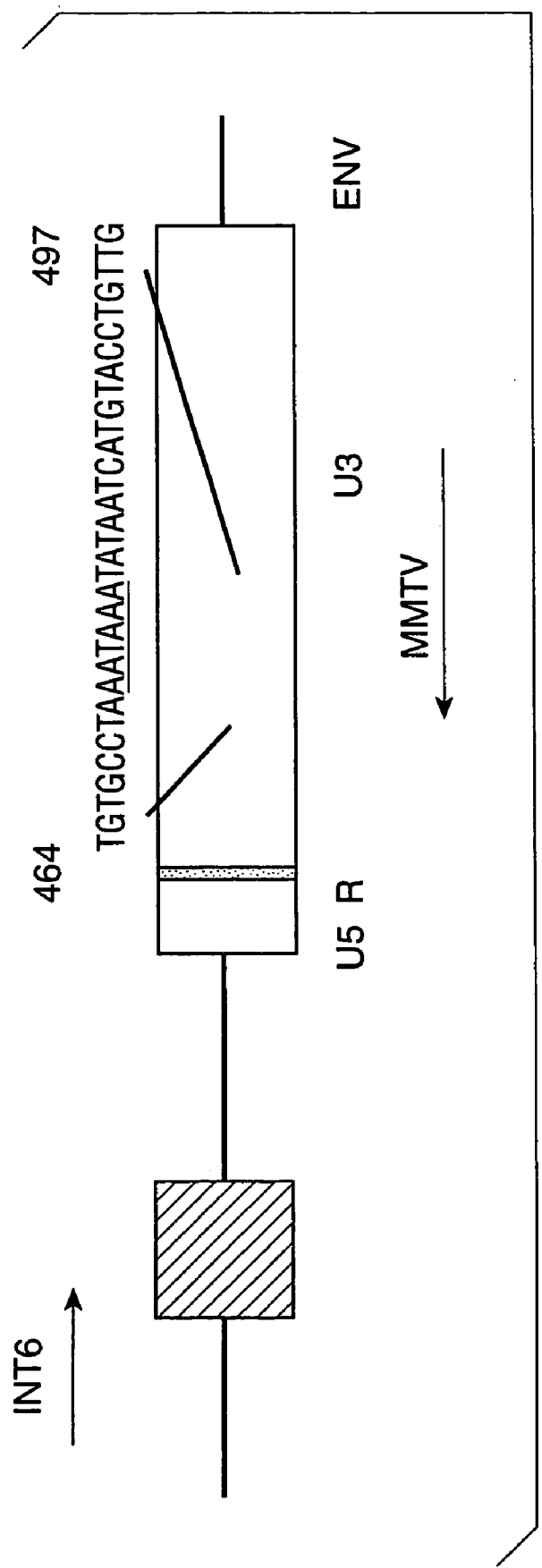
FIG. 8 shows a schematic illustrating the location and nucleotide sequence of a cryptic transcription stop signal (underlined) in the reverse sequence of the MMTV LTR where the sequence shown corresponds to bases 464 through 497 from the three prime end of the LTR. The hatched box corresponds to an Int6 exon and the open box corresponds to the LTR of an integrated MMTV proviral genome integrated within Int6. The U5, R and U3 regions of the MMTV LTR are indicated as well as the transcriptional orientations of the MMTV genome and the Int6 gene.

To test whether integration of MMTV into the Int6 gene produces altered RNA species, the nucleotide sequence of cDNA clones of Int6 RNA from tumor 1139 and tumor 22. In each case transcription of the rearranged allele resulted in the expression of a chimeric RNA species which terminated at a cryptic transcription stop signal in the reverse U3 portion of the MMTV LTR (FIG. 8). Of interest, a similar cryptic transcription termination signal has previously been shown to be active in certain MMTV induced rearrangements Fgf-3(Clausse, N., (1993) Virology, 194:157–165).

FIGS. 9A and 9B show the nucleotide-sequences of Int6-MMTV LTR RNA species detected in tumors 1139 (FIG. 9A) and 22 (FIG. 9B). In FIG. 9A, two RNA species from the rearranged allele (Figure A, 900 bp and 965 bp) were detected. The RNA species correspond to the 900 bp RNA species detected by Northern blot analysis in FIG. 4. In one RNA species exon 5 was spliced to the end of the U5 portion of the MMTV LTR and in the other species splicing occurred at a cryptic splice acceptor site in intron 5. Similarly, FIG. 9B, CZZ-1 there were three chimeric RNA species in which exon 9 was spliced to one of three different cryptic splice acceptor sites in intron 9. Since the size of the chimeric tumor RNA species is similar to that of the normal Int6 RNA, they went undetected in the Northern blot analysis of tumor 22 RNA FIG. 4.

Translation of the rearranged Int6 RNA species into putative proteins revealed that from all five species, the product is a truncated chimera of the Int6 amino acid sequences linked to novel amino acid sequences encoded by an Int6 intron and/or reverse MMTV LTR nucleotide sequences. The presence of the 965 bp RNA species in tumor 1139 suggests that truncation of the Int6 gene product is an important consequence of MMTV integration.

Example 9

Isolation of the Human Int6 Gene

Figure 10:
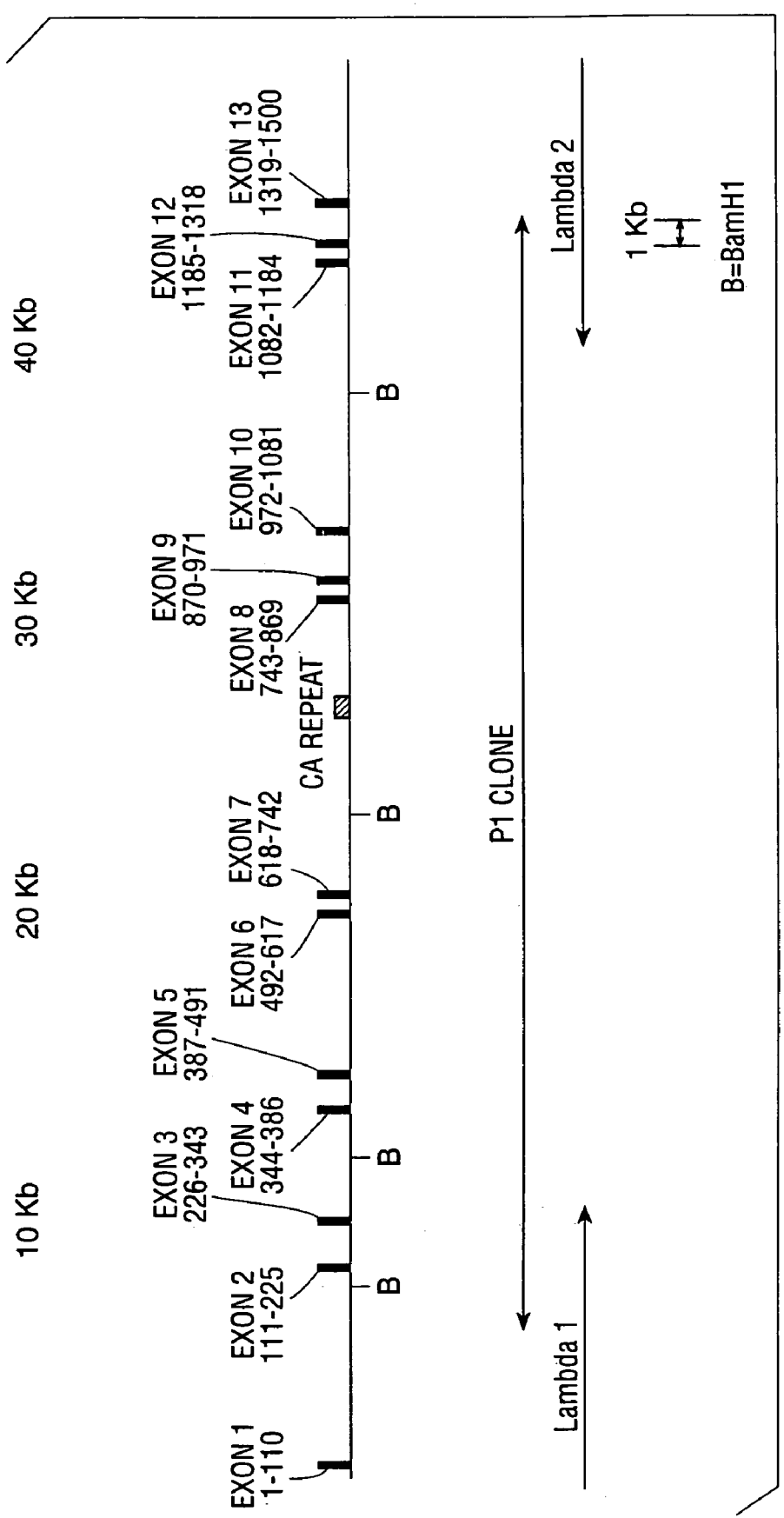
FIG. 10 shows the genomic map of the human Int6 gene. As in the mouse genome, the human Int6 gene is composed of 13 exons (filled bars) where the nucleotide boundaries for each exon are presented in the Figure. The location of a CA-repeat sequence in the seventh intron is also shown.
Figure 11:
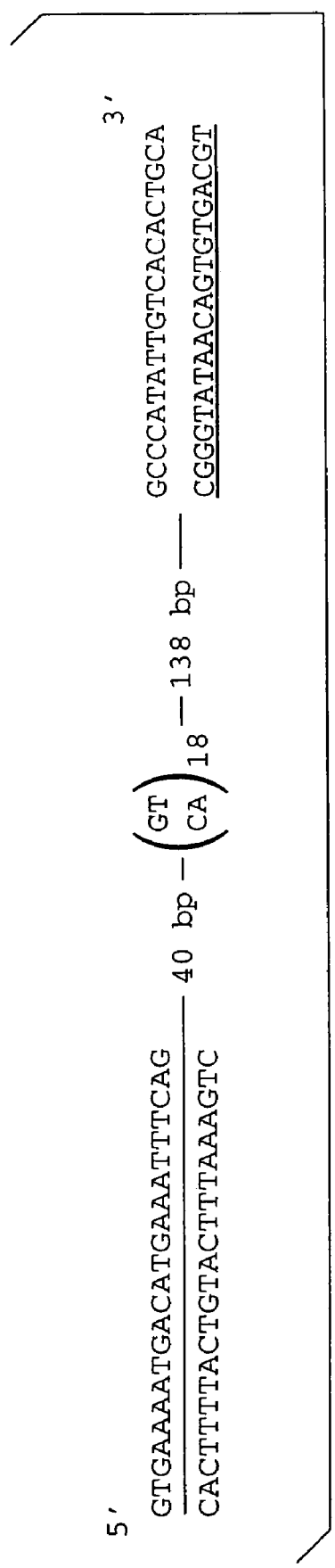
FIG. 11 shows the nucleotide sequence of primers (underlined, SEQ ID NO: 31) complementary to the nucleic acid sequences (not underlined, SEQ ID NO: 32) flanking the CA-repeat in intron 7 of the human Int6 gene. The distance of the primers from the CA-repeat are presented as 40 and 138 base pairs respectively and the number of CA-repeats (18) shown is that found in the wild-type Int6 gene. The upper nucleic acid sequences are shown in the 5' to 3' orientation and the lower nucleic acid sequences are shown in the 3' to 5' orientation reading left to right.

Mouse Int6 cDNA was used to probe a cDNA library of human lung RNA in lambda phage (Clontech Inc.) and using primers specific for the human Int6 cDNA (SEQ ID NO:3) cloned from the human lung cDNA library, a P1 phage library of human genomic DNA was screened by PCR for an Int6-related clone by Genome Systems Inc.(St. Louis, Mo.). Using this approach, a P1 phage clone and two lambda clones containing over 50 kb of human genomic DNA were obtained. Nucleotide sequence analysis of these clones revealed that the human Int6 gene is organized as shown in FIG. 10. As in the mouse genome, the human Int6 gene is composed of 13 exons. The human Int6 gene also contains a CA-repeat sequence in the seventh intron (FIG. 10).

Example 10

Size Polymorphism of the CA Reseat Sequence Contained in Intron 7

Primers complementary to the nucleic acid sequences flanking the CA-repeat in intron 7 of the human Int6 gene (FIG. 1) and having the sequences shown in SEQ ID NO:31 GTGAAAATGACATGAAATTTCAG and SEQ ID NO:32 TGCAGTGTGACAATATGGGC were used to PCR amplify the portion of the Int6 gene containing the CA-repeat in human genomic DNA. The conditions of the PCR were: 30 cycles of denaturation at 94° C. for one minute, annealing at 55° C. for one minute, and extension at 72° C. for two minutes. After the last cycle, there was an additional extension time of two minutes. Separation of the PCR products via non-denaturing 6% polyacrylamide gel electrophoresis revealed that 46 of the 84 individual DNAs analyzed were heterozygous (informative) for different size alleles.

Example 11

Chromosomal Localization of the Human Int 6 Gene

Figure 12:
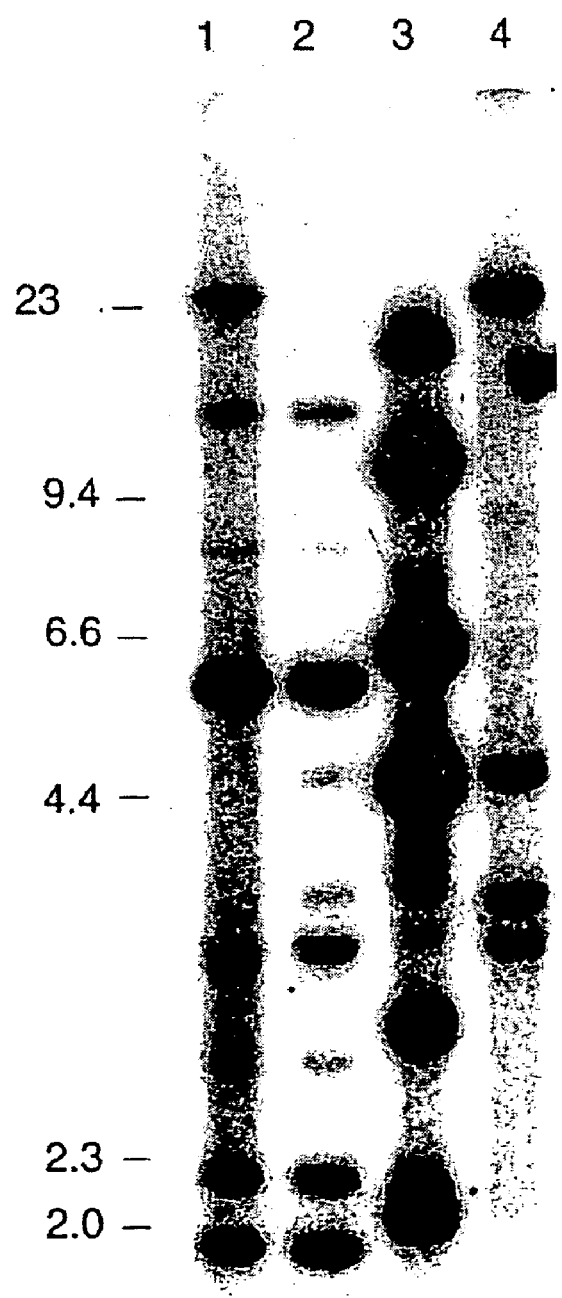
FIG. 12 shows the results of Southern blots in which human DNA (lane 4), Chinese hamster-human somatic cell hybrid DNA containing only human chromosome 6 (lane 1) or human chromosome 8 (lane 2) and mouse-human somatic cell hybrid DNA which contains human chromosomes 3, 7, 8, 15 and 17 (lane 3) were digested with Hind III and hybridized with human Int6 cDNA.

To determine the chromosomal localization of the human Int6 gene, Southern blot analysis of human DNA and DNA isolated from rodent-human somatic cell hybrids containing individual human chromosomes was performed. In brief, rodent-human somatic cell hybrid DNA or human DNA was digested with HindIII and hybridized with human Int6 cDNA at 37° C. for 24 hours in 3×SSPE, 5×Denhardt solution, 2.5% dextran sulfate and 40% formamide. The blot was then washed under stringent conditions involving three changes (each change done after twenty to thirty minutes) of 0.1×SSC and 0.5% SDS at 65° C. The results of this Southern blot are shown in FIG. 12 where lanes 1 and 2 contain Chinese hamster-human somatic cell hybrid DNA containing human chromosome 6 (lane 1) or 8 (lane 2), lane 3 contains DNA from mouse-human somatic cell hybrids containing human chromosomes 3, 7, 8, 15 and 17 and lane 4 contains human genomic DNA. The 23 kb fragment shown in lane 4 contains an Int6-related pseudogene and the coding sequences of the Int6 gene are defined by the 4.5, 3.5 and 3.0 kb fragments shown in lane 4. The results show that while the 23 kb fragment was detected only in lane 1 (hybrids containing human chromosome 6), the 4.5 and 3.5 kb fragments were detected in lane 2 (hybrids containing human chromosome 8). In addition, the 3.0 kb human fragment (see lane 4) was also detected in both lanes 1 and 2. However, the detection of the 3.0 kb fragment in lane 3 confirmed that the 3.0 kb fragment contains human Int6-related sequence rather than Chinese hamster sequence since mouse DNA was shown not to contain an Int6-related 3.0 kb Hind III fragment. These results demonstrate that the human Int6 gene is located on chromosome 8. This chromosomal localization was confirmed and further refined to chromosome 8q22-q24 by linkage analysis using the CA-repeat polymorphism described in Example 10.

Example 12

Figure 13:
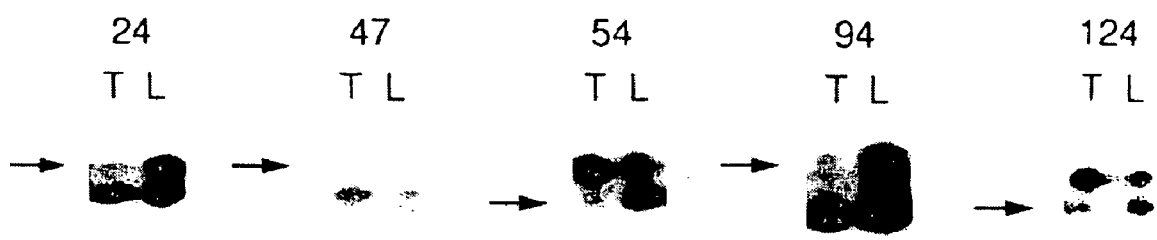
FIG. 13 shows the results of PCR amplification of DNA from primary human breast tumor (T) and matching normal tissue (L, where L indicates lymphocyte) using labelled primers flanking the CA repeat sequence in intron 7 of the Int6 gene. The numbers above each blot represent patients from which tumor and matching normal tissue samples were obtained. The arrow next to each blot indicates the complete loss, or a significantly reduced signal, of one allele relative to the matching normal DNA.

Detection of Mutations in the Int6 Gene in Human Breast Tumor DNA Resulting in a Loss of Heterozygosity Based on the results in MMTV-induced mouse mammary tumors presented earlier, DNA from human breast cancer biopsies was analyzed to determine whether the Int6 gene might be a target for mutation during malignant progression in human breast cancer. In brief, DNA from primary human breast tumor and from matching normal tissue of 40 individuals that were informative at the Int6 CA-repeat sequence were analyzed for evidence of loss of heterozygosity (LOH) in the tumor DNA via the PCR method utilized in Example 10. In eleven of these tumors (25%), there was either a complete loss or a significantly reduced signal of one allele relative to the matching normal DNA. Five of these eleven tumor DNAs (T) and their matching normal samples (L) are shown in FIG. 13. These results show that Int6 is a target for mutation during malignant progression in human breast cancer. Further, since Int6 gene expression has been detected in all tissues analyzed (see FIG. 7), mutation of the Int6 gene may occur during progression of cancers found in other tissues.

Example 13

Analysis of the Human Int6 Gene for Mututions by PCR-SSCP Using Primer Pairs Derived from Sequences Bounding Exons of the Int6 Gene Primer pairs complementary to nucleic acid sequences bounding 12 of the 13 human Int6 exons (FIG. 14) are shown as SEQ ID NOs:5–28. Using primer pairs selected from SEQ ID NOs:5–28, each of the exons of the Int6 gene except exon 7 were amplified from the eleven primary breast tumor DNAs having loss of heterozygosity at the Int6 gene (see Example 12) and from DNA of matching normal tissue samples by PCR and the PCR products were analyzed for single-stranded conformation polymorphism (SSCP) via denaturing polyacrylamide gel electrophoresis. Exon 7 was analyzed by hybrid mismatch methodology using the portion of human Int6 cDNA corresponding to exon 7. Analysis by both single strand conformation polymorphism analysis (SSCP) and hybrid mismatch methodologies of the primary breast tumor DNAs having loss of heterozygosity at the Int6 gene detected no point mutations in the remaining allele (data not shown). However, the promoter and intron regions of the remaining allele were not analyzed for mutations. Of course, if mutations of the promoter, intron and/or coding regions of the Int6 gene were detected in tumor samples, these mutations could be confirmed by nucleotide sequence analysis of the variant allele in the tumor-and-matching-normal tissue DNA.

Example 14

Loss of Expression of Int6 mRNA in Human Breast and Lung Tumor Samples

Total RNA isolated from 36 malignant human breast tumors, 2 preneoplastic lesions (high grade dysplasia) and matching normal tissue were surveyed for Int6 mRNA expression via Northern blot analysis using sequential hybridization with β-actin and human Int6 cDNA probes under conditions described in Gallahan and Callahan (*J. Virol.* 61:66–74 (1987)). Of these 38 samples, 14 (37%) exhibited significantly reduced or nondetectable Int6 mRNA expression as compared with matching normal tissue samples.

Figure 15:
FIG. 15 shows the results of a Northern blot of total RNA (20 μg each) isolated from primary breast tumor (T) and matching normal (N) tissue. The RNA samples were denatured in the presence of formaldehyde, run on 1% agarose gels containing formaldehyde, then transferred to a nylon membrane and hybridized sequentially with a β-actin-probe and a human Int6 cDNA probe.

Of these 14 cases, 8 were invasive ductal carcinomas (IDC), 2 were comedocarcinomas (IDC with a prevalent intraductal component), 2 were lobular carcinomas and 2 were the preneoplastic lesions. A representative Northern blot is shown in FIG. 15.

Figure 16:
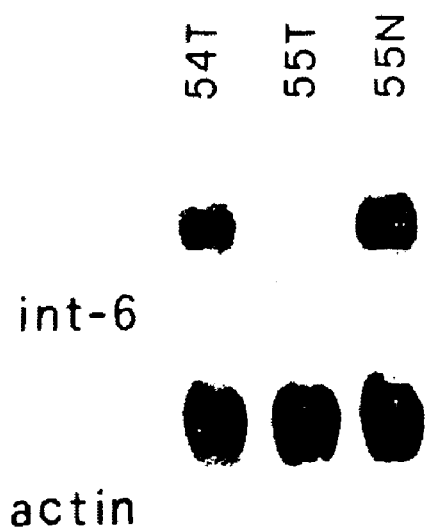
FIG. 16 shows the results of a Northern blot of total RNA (20 μg each) isolated from human nonsmall cell lung carcinomas (54T and 55T) and matching normal tissue (55N). Matching normal tissue for 54T was also surveyed for Int6 mRNA expression but the Northern blot for 54N is not shown. Northern blot analysis was carried out as described in FIG. 15.

In a separate study, Int6 mRNA expression in 47 nonsmall cell lung carcinomas (NSCLC) and matching normal tissues was surveyed via Northern analysis of 10 μg total RNA as described above in this Example. A representative Northern blot is shown in FIG. 16 and the results of the Northern analyses of the 47 NSCLC samples are summarized in Table 1.

TABLE 1

ASSOCIATIONS BETWEEN LOSS OF EXPRESSION
OF Int6 AND CLINICAL PARAMETERS

| HISTOTYPE | REDUCED OR NONDETECTABLE EXPRESSION | NORMAL EXPRESSION | TOTAL SAMPLES | P VALUE |
|---|---|---|---|---|
| SQUAMOUS CELL | 3(14%) | 18 | 21 | |
| ADENOCARCINOMA | 8(67%) | 4 | 12 | 0.003 |
| BRONCHIOLOALVEOLAR | 2(33%) | 4 | 6 | |

Of interest, 14 of 47 NSCLCs showed loss of Int6 mRNA expression and loss of Int6 mRNA expression was observed to have a highly significant association (P=0.003) with a particular histologic subtype (Table 1, adenocarcinoma of NSCLC).

The results presented in this Example are consistent with the conclusion that loss of Int6 expression is an early event in human breast cancer and a contributing factor in other neoplasias such as those of the lung.

Example 15

Characterization of the Murine Int6 Protein

The Int6 gene encodes a 50 kD protein with three potential translation start sites (at 27 bp, 174 bp and 189 bp of the mouse sequence). Each of these polypeptides were detected as products of in vitro translation of Int6 RNA in the rabbit reticulocyte system. Rabbit polyclonal sera to synthetic peptides corresponding to amino acid residues 57–71 (peptide 47) and 262–281 (peptide 20) of mouse Int6 were prepared and used to immunoprecipitate the Int6 in vitro translation products. This immunoprecipitation was competed by the corresponding peptide. Western blot analysis of protein extracts of adult mouse tissues (brain, lung, kidney, muscle, heart and mammary gland), using antibodies to peptide 20 (rAB 20), detected a major 40 KD polypeptide as well as a triplet of 80 KD polypeptides. Reaction with these polypeptides was competed with peptide 20. Of interest, expression of a 30 KD Int6 related polypeptide was also observed in Western blots of salivary gland extracts. It is believed that the 40 KD polypeptide may represent a cleavage product of the 50 KD precursor and that the 80 KD cross reacting polypeptide may represent dimers of the 40 KD polypeptides.

In addition, cell fractionation studies and immunofluorescence studies using antibodies to the above peptides have demonstrated that Int6 is primarily localized to the cytoplasm. Moreover, in immunofluorescence studies of mouse embryos, the Int6 protein was localized to the golgi apparatus.

Finally, Int6 protein, which contains three candidate protein kinase C (PKC) phosphorylation sites, was expressed in bacteria using the QUIA Express Type 4 vector (Quiagen, Chatsworth Calif.), purified and shown to be phosphorylated by PKC (data not shown).

We claim:

1. A purified antibody or fragment thereof that specifically binds SEQ ID NO: 4, or a fragment of about 20 to about 24 consecutive amino acids of SEQ ID NO: 4.

2. The purified antibody of claim 1, wherein the antibody is a monoclonal antibody.

3. The purified antibody of claim 2, wherein the antibody is a humanized antibody.

4. The purified antibody of claim 1, covalently linked to a toxin, radionucleotide, detectable label or drug.

5. The isolated antibody of claim 4, covalently linked to a toxin.

6. The purified antibody of claim 4, covalently linked to a radionucleotide.

7. The purified antibody of claim 4, covalently linked to a detectable label.

8. The purified antibody of claim 1, wherein the antibody is a polyclonal antibody.

9. The purified antibody of claim 1, wherein the antibody specifically binds to a polypeptide encoded by a cDNA deposited as ATCC Accession No. 97209 or as ATCC Accession No. 97030.

10. A kit, comprising a container containing the purified antibody of claim 1.

11. The kit of claim 10, further comprising a container comprising a second antibody that specifically binds the purified antibody that specifically binds SEQ ID NO:4, wherein the second antibody comprises a label.

12. An isolated antibody that specifically binds amino acids 262–281 or amino acids 57–71 of SEQ ID NO: 4.

* * * * *